US008378124B2

(12) United States Patent
Nugent et al.

(10) Patent No.: US 8,378,124 B2
(45) Date of Patent: Feb. 19, 2013

(54) PREPARATION OF PROTECTED ALPHA-KETO BETA-AMINO ESTERS AND AMIDES

(75) Inventors: William A. Nugent, Cambridge, MA (US); Adam R. Looker, Cambridge, MA (US); Raymond E. Forslund, Natick, MA (US); Theodore A. Martinot, Jamaica Plain, MA (US); Cristian L. Harrison, Beverly, MA (US); Shereen Ibrahim, Cambridge, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 12/982,209

(22) Filed: Dec. 30, 2010

(65) Prior Publication Data

US 2011/0213161 A1    Sep. 1, 2011

Related U.S. Application Data

(63) Continuation of application No. PCT/US2009/003940, filed on Jul. 2, 2009.

(60) Provisional application No. 61/078,059, filed on Jul. 3, 2008.

(51) Int. Cl.
*C07D 339/06* (2006.01)
(52) U.S. Cl. .......................................... 549/39
(58) Field of Classification Search ..................... 549/39
See application file for complete search history.

(56) References Cited

U.S. PATENT DOCUMENTS

| 5,514,694 | A | 5/1996 | Powers et al. |
| 5,610,297 | A | 3/1997 | Powers |
| 6,235,929 | B1 * | 5/2001 | Powers ........................ 562/450 |
| 2005/0059800 | A1 * | 3/2005 | Sudhakar et al. ............. 530/331 |
| 2007/0032433 | A1 * | 2/2007 | Saksena et al. ................ 514/18 |

OTHER PUBLICATIONS

Beevers, Solution and Solid-Phase Synthesis of Potent Inhibitors of Hepatitis C Virus NS3 Proteinase, 2002, Bioorganic & Medicinal Chemistry Letters, vol. 12, p. 641-643.*
Ellman, Applications of tert-butanesulfinamide in the asymmetric synthesis of amines, 2003, Pure Appl. Chem. vol. 75, No. 1, p. 39-46.*
Harmata, Expedient Synthesis of Sulfinamides from Sulfonyl Chlorides, 2007, J. Org. Chem. vol. 72, p. 683-685.*
Lee, A practical diastersoselective synthesis of β-amino-α-hydroxy carboxylates, 2003, Tetrahedron:Asymmetry, p. 3639-3641.*
Ocain, α-Keto Amide Inhibitors of Aminopeptidases, 1992, J. Med. Chem, vol. 35, p. 451-456.*
International Search Report for PCT/US2009/003940 dated Oct. 30, 2009.
Davis, et al., "alpha-Amino 1,3-dithioketal mediated asymmetric synthesis of piperidines (L-733,060) and tetrahydrofuran glycines," Tetrahedron Letters, Elsevier, Amsterdam, Dec. 2007, vol. 49, No. 5, pp. 870-872, XP022413163.
Papanikos, A., et al., "alpha-Keto Amide Peptides: A Synthetic Strategy to Resin-Bound Peptide Isosteres for Protease Inhibitor Screening on Solid Support," Journal of Combinatorial Chemistry, 2004, vol. 6, No. 2, pp. 181-195, XP002553143.
Zhaozhao, Li, et al., "Peptide alpha-Keto ester, alpha-Keto amide, and alpha-Keto acid inhibitors of calpains and other cysteine proteases," Journal of Medicinal Chemistry, American Chemical Society, Washington, US, Oct. 1993, vol. 36, No. 22, pp. 3472-3480, XP000565670.

* cited by examiner

*Primary Examiner* — Golam M M Shameem
*Assistant Examiner* — Karen Cheng
(74) *Attorney, Agent, or Firm* — Honigman Miller Schwartz and Cohn LLP; Heidi M. Berven; Jonathan P. O'Brien

(57) ABSTRACT

The invention provides β-sulfonamide α-keto esters and amides in which the α-keto is protected as a 1,3-dithiolane derivative. Also provided are methods for preparing such esters and amides and for incorporating them into peptides.

7 Claims, No Drawings

PREPARATION OF PROTECTED ALPHA-KETO BETA-AMINO ESTERS AND AMIDES

CROSS-REFERENCE

This application is a continuation of PCT Application No. PCT/US2009/003940, filed Jul. 2, 2009, which claims priority of U.S. Application No. 61/078,059 filed Jul. 3, 2008. Both of these documents are incorporated herein in their entirety.

BACKGROUND OF THE INVENTION

Peptidyl alpha-keto esters and alpha-keto amides are broadly useful in medicinal chemistry as potent inhibitors of proteolytic enzymes such as serine and cysteine proteases. Their cellular targets include calpain (a calcium-activated cysteine protease that has been implicated in stroke, Alzheimer's disease and muscular dystrophy), caspase (a cysteine protease that plays a role in apoptosis), and thrombin (a serine protease that converts fibrinogen to fibrin). In particular, beta-amino alpha-keto amide isosteres are of interest as viral protease inhibitors for the treatment of HIV and hepatitis C.

Conventional routes to beta-amino alpha-keto amides invariably rely on the one-carbon homologation of an N-protected alpha-amino acid derivative. A process using cyanide as the one-carbon addend has been described by Manoz et al. in *Bioorg. Med. Chem.*, 2, 1085-1090 (1994). In this example, epimerization occurs at the nitrogen-bearing carbon during the subsequent oxidation step, affording the alpha-keto amide as a 1:1 mixture of diastereomers. In contrast, a stereospecific process involving the addition of an isonitrile to an N-protected alpha-amino aldehyde has been described by Banfi et al. in *Tetrahedron Lett.*, 43, 4067-4069 (2002). A second stereospecific process involves the addition of (cyanomethylene)phosphorane to an amino acid derivative, as described by Wasserman et al. in *J. Org. Chem.*, 62, 8972-8973 (1997). This route initially provides an acyl cyanophosphorane intermediate A which is converted to the beta-keto amide product B upon ozonolysis and treatment with a primary amine.

These one-carbon homologation routes are most useful when the required alpha-amino acid is a readily available "natural" amino acid. However, a general limitation occurs when the requisite starting material is an "unnatural" (non-proteinaceous) amino acid. Such amino acids are themselves prepared by expensive multi-step synthetic sequences and in some case are not available in sufficient quantities to support commercial drug manufacture.

An additional problem is the sensitivity of the beta-amino alpha-keto amide functionality toward both acidic and basic reagents. This can interfere with incorporation of the molecule into a peptide. A solution to this problem is described by Papanikos et al. in *J. Combin. Chem.*, 6, 181-195 (2004). In this process, a beta-amino alpha-keto amide is first synthesized in enantiomerically pure form and is then protected as a 1,3-dithiolane derivative in a separate step. After incorporation into a peptide, the dithiolane functional group is removed, unmasking the alpha-keto amide functionality.

A related approach is described by Powers et al. in *J. Med. Chem.*, 36, 3472-3480 (1993). In Powers' approach, an alpha-keto ester is first protected as a dithiolane derivative and is then converted to an alpha-keto amide in subsequent transformations. However, this process is not stereospecific.

As is clear from the above discussion, it would be advantageous to access enantiomerically pure dithiolane-protected alpha-keto amides via a route that does not require the availability of the corresponding alpha-amino acid.

A process for enantioselective addition of a 6-membered ring dithiane derivative to an enantiomerically pure sulfinimine has been described by Davis et al. in *Tetrahedron Lett.*, 49, 870-872 (2008). However, this reaction fails when the substituent on the carbon atom between the two sulfur atoms in the dithiane derivative is an electron-withdrawing functional group, e.g., an ester or amide group.

BRIEF DESCRIPTION OF THE INVENTION

In general, the present invention relates to enantiomerically pure beta-amino alpha-keto (i.e., β-amino α-keto) esters, amides, and acids, and methods for preparing them. These compounds, described and shown herein as Formulae I, IV, V, and VI, may be useful for making α-keto-containing peptidyl compounds shown herein as Formulae VII and VIII.

In one aspect, the present invention provides a process for preparing an enantiomerically pure, alpha-keto beta-sulfinamido ester protected as a 1,3-dithiolane derivative having Formula $(S,S_s)$-I or $(R,R_s)$-I.

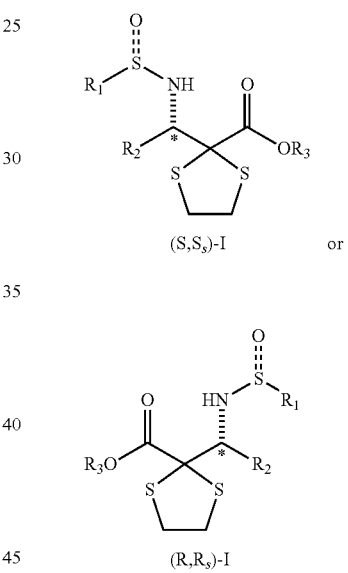

In Formula $(S,S_s)$-I or $(R,R_s)$-I, $R_1$ and $R_3$ are each independently alkyl or aryl; and $R_2$ is alkyl, cycloalkyl, alkenyl, aryl, or heterocycloalkyl bonded to the nitrogen-bearing carbon atom (i.e., C*) of Formula I at any available ring carbon atom. The process includes mixing an enantiomerically pure sulfinimine of Formula $(S_s)$-II or $(R_s)$-II

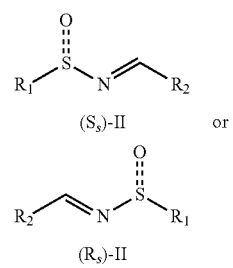

with a dithiolane carboxylate ester of Formula III

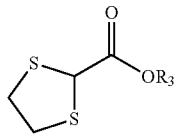

in the presence of a base of sufficient strength to deprotonate the dithiolane hydrogen of Formula III, wherein $R_1$ and $R_2$ in Formula II and $R_3$ in Formula III are as defined above for Formula I, to produce the alpha-keto beta-sulfinamido ester of Formula $(S,S_s)$-I or $(R,R_s)$-I.

In another aspect, the invention provides a process for preparing an enantiomerically pure β-sulfinamide α-keto amide of Formula $(S,S_s)$-IV or $(R,R_s)$-IV.

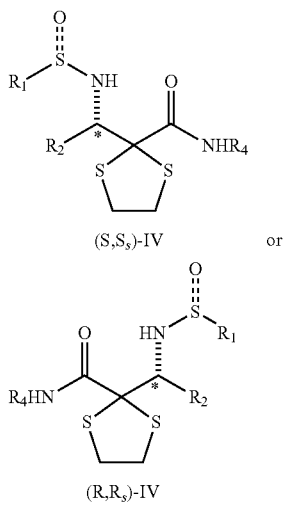

In Formula $(S,S_s)$-IV or $(R,R_s)$-IV, $R_1$ is alkyl or aryl; $R_2$ is alkyl, cycloalkyl, (cycloalkyl)alkyl, alkenyl, aryl, or heterocycloalkyl bonded to the carbon atom C* at a ring carbon atom; and $R_4$ is hydrogen, alkyl, cycloalkyl, or aryl. This process includes mixing the compound of Formula $(S,S_s)$-I or $(R,R_s)$-I:

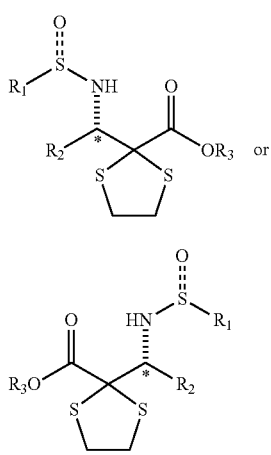

with an amine of the formula $R_4NH_2$, wherein $R_1$, $R_2$, and $R_4$ are as defined above and $R_3$ in the compound of Formula $(S,S_s)$-I or $(R,R_s)$-I is alkyl or aryl, to produce the β-sulfinamide α-keto amide of Formula $(S,S_s)$-IV or $(R,R_s)$-IV.

Alternatively, the process for preparing an enantiomerically pure β-sulfinamide α-keto amide of Formula $(S,S_s)$-IV or $(R,R_s)$-IV can be carried out by:

a) mixing the compound of Formula $(S,S_s)$-I or $(R,R_s)$-I with an aqueous base solution optionally in the presence of a co-solvent;

b) neutralizing the solution to provide a carboxylic acid of Formula $(S,S_s)$-V or $(R,R_s)$-V;

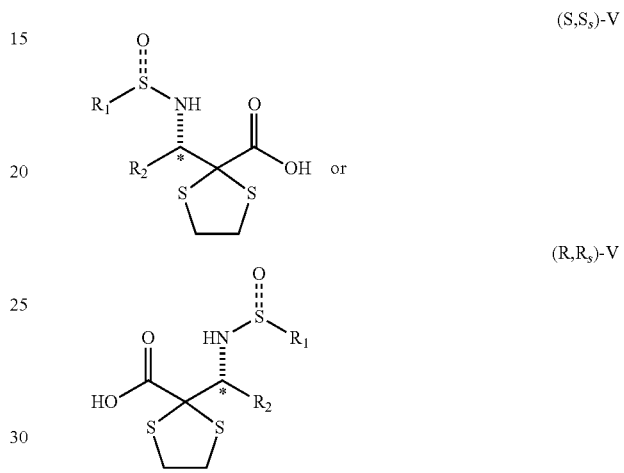

and c) mixing the carboxylic acid of Formula $(S,S_s)$-V or $(R,R_s)$-V with an amine $R_4NH_2$, wherein $R_4$ is as defined above, to provide the pure β-sulfinamide α-keto amide of Formula $(S,S_s)$-IV or $(R,R_s)$-IV.

In yet another aspect, the present invention provides a method for preparing a β-sulfonamide α-keto amide of Formula $(S,S_s)$-IV or $(R,R_s)$-IV. The method includes a) mixing a sulfinimine of Formula $(S_s)$-II or $(R_s)$-II with a dithiolane carboxylate ester of Formula III, in the presence of a base of sufficient strength to deprotonate the dithiolane hydrogen of Formula III, to give a β-sulfonamide α-keto ester of Formula $(S,S_s)$-I or $(R,R_s)$-I; and b) mixing the β-sulfonamide α-keto ester of Formula $(S,S_s)$-I or $(R,R_s)$-I with an amine of the formula $R_4NH_2$ to give the β-sulfonamide α-keto amide of Formula $(S,S_s)$-IV or $(R,R_s)$-IV; or mixing the β-sulfonamide α-keto ester of Formula $(S,S_s)$-I or $(R,R_s)$-I with an aqueous base solution optionally in the presence of a co-solvent, neutralizing the solution to provide a carboxylic acid of Formula $(S,S_s)$-V or $(R,R_s)$-V, and mixing the carboxylic acid of Formula $(S,S_s)$-V or $(R,R_s)$-V with an amine $R_4NH_2$, wherein $R_4$ is as defined above, to provide the β-sulfonamide α-keto amide of Formula $(S,S_s)$-IV or $(R,R_s)$-IV.

Still another further aspect of the present invention provides a process for coupling an amide of Formula $(S,S_s)$-IV or $(R,R_s)$-IV to a peptide containing a carboxylic acid terminus (HOOC-Pep.). This process includes mixing a solution of the amide $(S,S_s)$-IV or $(R,R_s)$-IV with a mineral acid to provide a compound of Formula (S)-VI or (R)-VI:

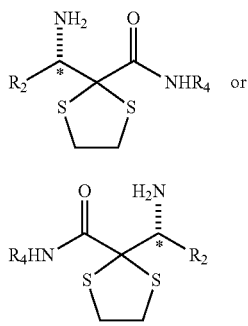

(S)-VI

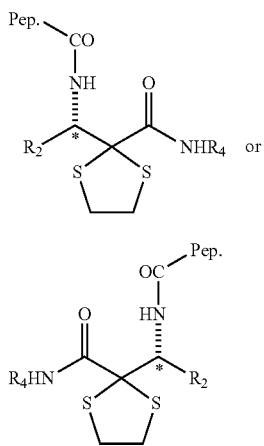

(R)-VI wherein $R_1$ is as defined above; mixing the compound of Formula (S)-VI or (R)-VI with the carboxylic acid terminus of the peptide optionally in the presence of a coupling agent to give a compound of Formula (S)-VII or (R)-VII;

(S)-VII (R)-VII

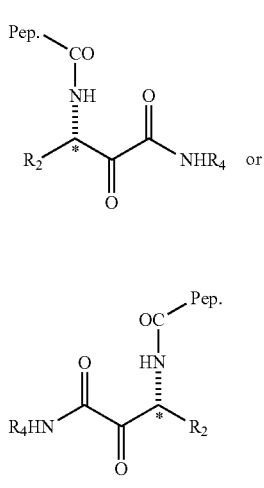

and removing the 1,3-dithiolane protecting group in the compound of Formula (S)-VII or (R)-VII in the presence of an oxidant to provide a peptide of Formula (S)-VIII or (R)-VIII:

(S)-VIII (R)-VIII containing a β-amino α-keto amide functionality.

Also within the scope of the present invention are compounds of Formula I, Formula IV, or Formula VI:

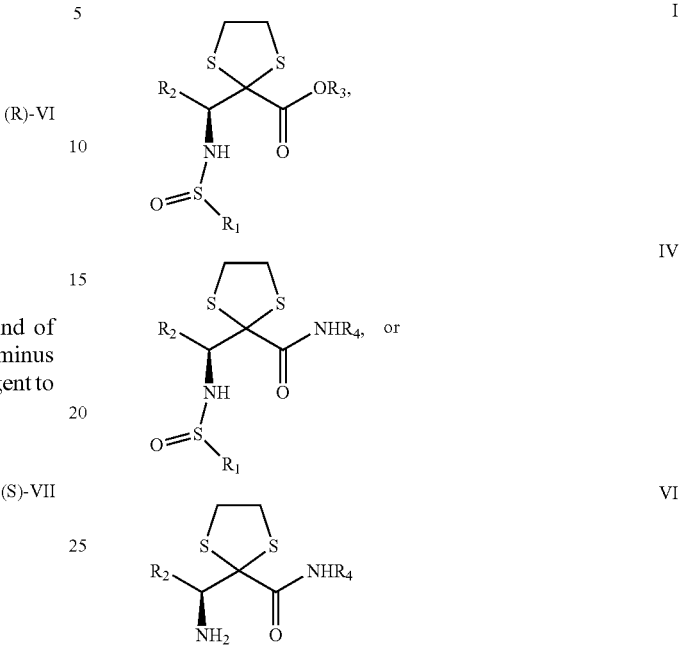

I

IV

VI

The variables in these formulae, i.e., $R_1$, $R_2$, $R_3$, and $R_4$, are provided herein.

The present invention is partially based on the discovery that by a mere reduction of the ester-substituted dithiane ring by only one carbon atom (i.e., changing the ring size of the addend from the 6-membered dithiane with an ester substituent to a 5-membered ring dithiolane), addition to enantiomerically pure sulfinimines proceeds readily, to provide protected alpha-keto beta-amino ester as a single or enantiomerically pure diastereomer with high selectivity (generally greater than 85%, e.g., 90% or 99%).

DETAILED DESCRIPTION OF THE INVENTION

In one aspect, the present invention provides a process for preparing an enantiomerically pure, α-keto β-sulfinamido ester of Formula (S,S$_s$)-I or (R,R$_s$)-I (in which the α-keto is protected as a 1,3-dithiolane derivative).

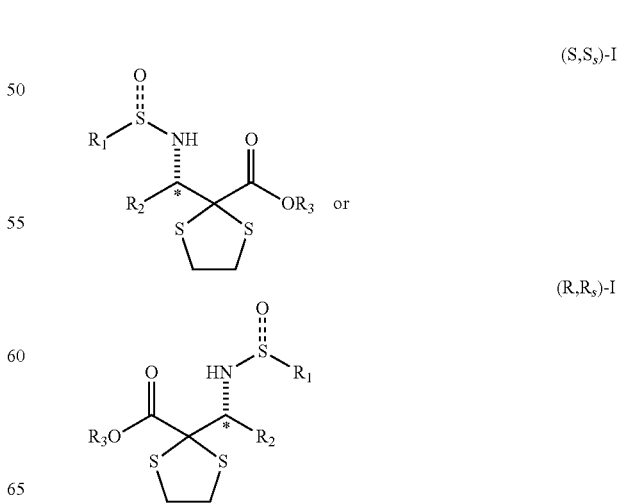

(S,S$_s$)-I (R,R$_s$)-I

In Formula $(S,S_s)$-I or $(R,R_s)$-I, $R_1$ and $R_3$ are each independently alkyl or aryl; and $R_2$ is alkyl, cycloalkyl, alkenyl, aryl, or heterocycloalkyl bonded to the nitrogen-bearing carbon atom (i.e., C*) of Formula I at any available ring carbon atom. The process includes mixing an enantiomerically pure sulfinimine of Formula $(S_s)$-II or $(R_s)$-II

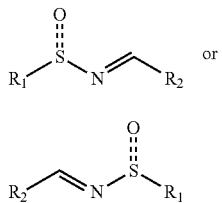

$(S,S_s)$-II or

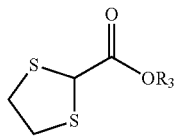

$(R,R_s)$-II with a dithiolane carboxylate ester of Formula III

III

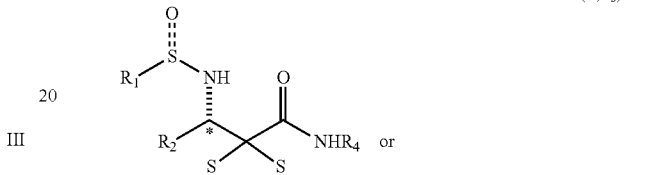

in the presence of a base of sufficient strength to deprotonate the dithiolane hydrogen of Formula III, wherein $R_1$ and $R_2$ in Formula II and $R_3$ in Formula III are as defined above for Formula I, to give the α-keto β-sulfinamido ester of Formula $(S,S_s)$-I or $(R,R_s)$-I.

A compound of Formula II with the S configuration on the sulfur atom gives rise to a compound of Formula I which retains the S configuration at sulfur and additionally has the S configuration on the nitrogen-bearing carbon atom. A compound of Formula II with the R configuration on the sulfur atom gives rise to a compound of Formula I which retains the R configuration on sulfur and additionally has the R configuration at the nitrogen-bearing carbon atom. This is to say that the stereogenic center on the sulfur atom induces the stereochemistry on the carbon atom.

In some embodiments, the product of the process of this invention is dominantly (i.e., at least 85%, e.g., 95% or 99%) a single $(R,R_s)$ or $(S,S_s)$ diastereomer. For example, at least 95% or at least 99% of the product may be a single $(R,R_s)$ or $(S,S_s)$ diastereomer.

In some embodiments, the reaction between a compound of Formula II and a compound Formula III is carried out in a solvent selected from the group consisting of tetrahydrofuran (THF), 2-methyltetrahydrofuran, ethanol, methanol, and dioxane, or mixtures thereof.

In some embodiments, the reaction between compounds of Formula II and Formula III is in the presence of a base containing, e.g., lithium, potassium, or sodium. Examples of such a base include, but are not limited to, lithium hexamethyldisilamide, hexynyllithium, lithium diisoprolyamide, lithium bis(trimethylsilyl)amide, sodium hexamethyldisilamide, sodium bis(trimethylsilyl)amide, sodium hydride, potassium bis(trimethylsilyl)amide, potassium hexamethyldisilamide, potassium hydride, potassium tert-butoxide, or potassium tert-amyloxide.

In some embodiments, $R_1$ is optionally substituted phenyl (e.g., substituted with an alkyl such as methyl). In some further embodiments, $R_1$ is methylphenyl (e.g., p-methylphenyl).

In some embodiments, $R_1$ is alkyl. Examples of suitable $R_1$ include, but are not limited to, methyl, ethyl, propyl, isopropyl, butyl, and tert-butyl.

In some embodiments, $R_2$ is alkyl, (cycloalkyl)alkyl, or aryl. Examples of suitable $R_2$ include, but are not limited to, $C_{1-8}$ or $C_{1-4}$ alkyl (e.g., methyl, ethyl, propyl, isopropyl, butyl, isobutyl, or tert-butyl), (cyclopropyl)methyl, or naphthyl.

In some embodiments, $R_3$ is alkyl (e.g., $C_{1-8}$ or $C_{1-4}$ alkyl). Examples of suitable $R_3$ include, but are not limited to, methyl, ethyl, propyl, isopropyl, or tert-butyl.

In another aspect, the invention provides a process for preparing an enantiomerically pure β-sulfinamide α-keto amide of Formula $(S,S_s)$-IV or $(R,R_s)$-IV.

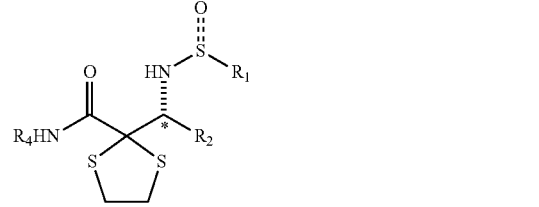

$(S,S_s)$-IV or

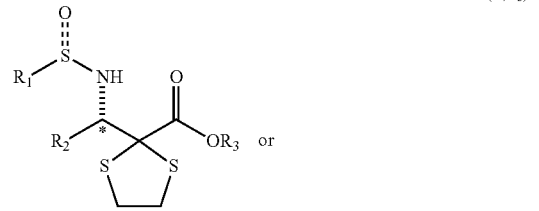

$(R,R_s)$-IV

In Formula $(S,S_s)$-IV or $(R,R_s)$-IV shown above, the α-keto group is protected as a 1,3-dithiolane derivative; $R_1$ is alkyl or aryl; $R_2$ is alkyl, cycloalkyl, (cycloalkyl)alkyl, alkenyl, aryl, or heterocycloalkyl bonded to the carbon atom C* at a ring carbon atom; and $R_4$ is hydrogen, alkyl, cycloalkyl, or aryl. This process includes mixing the compound of Formula $(S,S_s)$-I or $(R,R_s)$-I:

$(S,S_s)$-I or

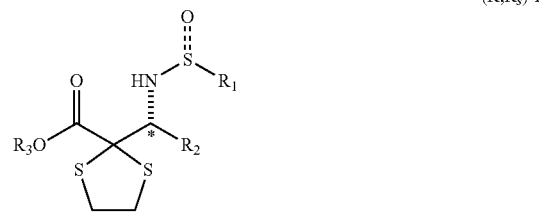

$(R,R_s)$-I with an amine of the formula $R_4NH_2$, wherein $R_1$, $R_2$, and $R_4$ are as defined above, and $R_3$ in the compound of Formula $(S,S_s)$-I or $(R,R_s)$-I is alkyl or aryl.

In some embodiments, the reaction between the compound of Formula (I) and the amine is carried out in an alcohol or an alcohol mixture. In some further embodiments, the alcohol is propanol, ethanol, or methanol, or a mixture (i.e., co-solvent) thereof (e.g., a 50/50 or 40/60 mixture of methanol or ethanol).

In some embodiments, $R_1$ is an optionally substituted phenyl. In some further embodiments, the phenyl is substituted with a $C_{1-8}$ or $C_{1-4}$ alkyl, such as methyl or ethyl.

In some further embodiments, $R_1$ is methylphenyl. In some further embodiments, $R_1$ is p-methylphenyl.

In some embodiments, $R_1$ is $C_{1-8}$ or $C_{1-4}$ alkyl. In some further embodiments, $R_1$ is methyl, ethyl, propyl, isopropyl, butyl, or tert-butyl.

In some embodiments, $R_2$ is alkyl (e.g., $C_{1-8}$ or $C_{1-4}$ alkyl), (cycloalkyl)alkyl, or aryl. Examples of suitable $R_2$ include, but are not limited to, methyl, ethyl, propyl, isopropyl, butyl, isobutyl, tert-butyl, (cyclopropyl)methyl, or naphthyl.

In some embodiments, $R_4$ is alkyl (e.g., $C_{1-8}$ or $C_{1-4}$ alkyl) or cycloalkyl. In some further embodiments, $R_4$ is methyl, ethyl, or cyclopropyl.

A further aspect of this invention relates to an alternative method for preparing an enantiomerically pure β-sulfinamide α-keto amide of Formula $(S,S_s)$-IV or $(R,R_s)$-IV.

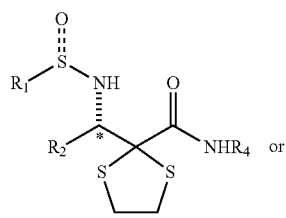

$(S,S_s)$-IV

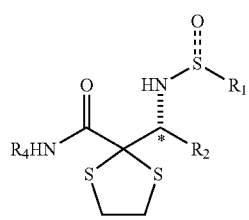

$(R,R_s)$-IV

In Formulae $(S,S_s)$-IV or $(R,R_s)$-IV, the α-keto group is protected as a 1,3-dithiolane derivative; $R_1$ is alkyl or aryl; $R_2$ is alkyl, cycloalkyl, (cycloalkyl)alkyl, alkenyl, aryl, or heterocycloalkyl bonded to the carbon atom C* at a ring carbon atom; and $R_4$ is hydrogen, alkyl, cycloalkyl, or aryl.

This alternative method includes reacting the compound of Formula $(S,S_s)$-I or $(R,R_s)$-I (wherein $R_1$ and $R_2$ are as defined above; and $R_3$ is alkyl or aryl):

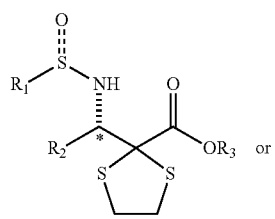

$(S,S_s)$-I

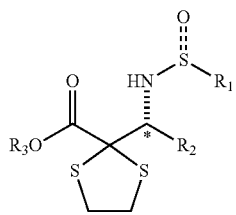

$(R,R_s)$-I with an aqueous base solution optionally in the presence of a co-solvent, and then neutralizing the solution to provide a carboxylic acid of Formula $(S,S_s)$-V or $(R,R_s)$-V;

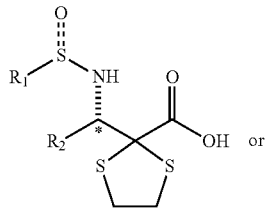

$(S,S_s)$-V

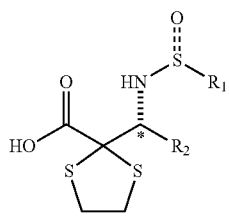

$(R,R_s)$-V and reacting the carboxylic acid of Formula $(S,S_s)$-V or $(R,R_s)$-V with an amine $R_4NH_2$ (wherein $R_4$ is as defined herein) to provide the β-sulfinamide α-keto amide of Formula $(S,S_s)$-IV or $(R,R_s)$-IV.

In some embodiments of this alternative method, at least 95% (e.g., 99% or 99.9%) of the product (i.e., the β-sulfinamide α-keto amide of Formula $(S,S_s)$-IV or $(R,R_s)$-IV) is a single $(S,S_s)$ or $(R,R_s)$ enantiomer.

In some other embodiments, the co-solvent is an alcohol, dioxane, or THF, or a mixture thereof (including a mixture of different alcohols). In some further embodiments, the alcohol is propanol, ethanol, or methanol, or a mixture thereof (e.g., a 50/50 or 40/60 mixture of methanol or ethanol).

In some other embodiments, $R_1$ is an optionally substituted phenyl. In some further embodiments, the phenyl is substituted with a $C_{1-8}$ or $C_{1-4}$ alkyl, such as methyl or ethyl.

In some further embodiments, $R_1$ is methylphenyl. In some further embodiments, $R_1$ is p-methylphenyl.

In some embodiments, $R_1$ is $C_{1-8}$ or $C_{1-4}$ alkyl. In some further embodiments, $R_1$ is methyl, ethyl, propyl, isopropyl, butyl, or tert-butyl.

In some embodiments, $R_2$ is alkyl (e.g., $C_{1-8}$ or $C_{1-4}$ alkyl), (cycloalkyl)alkyl, or aryl. Examples of suitable $R_2$ include, but are not limited to, methyl, ethyl, propyl, isopropyl, butyl, isobutyl, tert-butyl, (cyclopropyl)methyl, or naphthyl.

In some embodiments, $R_4$ is alkyl (e.g., $C_{1-8}$ or $C_{1-4}$ alkyl) or cycloalkyl. In some further embodiments, $R_4$ is methyl, ethyl, or cyclopropyl.

The invention further provides a method for coupling an amide of Formula (S,S$_s$)-IV or (R,R$_s$)-IV:

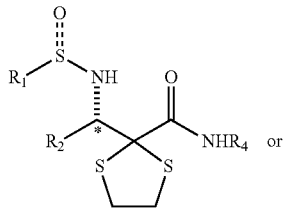

(S,S$_s$)-IV or

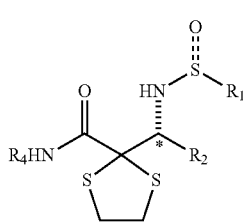

(R,R$_s$)-IV to a peptide containing a carboxylic acid terminus (HOOC-Pep.), wherein the α-keto group is protected as a 1,3-dithiolane derivative; R$_1$ is alkyl or aryl; R$_2$ is alkyl, cycloalkyl, (cycloalkyl)alkyl, alkenyl, aryl, or heterocycloalkyl bonded to the carbon atom C* at a ring carbon atom; and R$_4$ is hydrogen, alkyl, cycloalkyl, or aryl.

This method includes treating a solution of the amide (S,S$_s$)-IV or (R,R$_s$)-IV with a mineral acid to provide a compound of Formula (S)-VI or (R)-VI

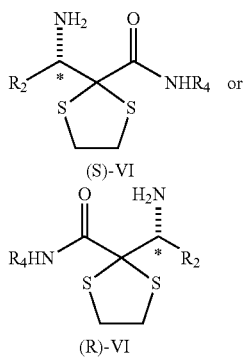

(wherein R$_1$ is as defined herein), reacting the compound of Formula (S)-VI or (R)-VI with the carboxylic acid terminus of the peptide or amino acid in the presence of a coupling agent to give a compound of Formula (S)-VII or (R)-VII:

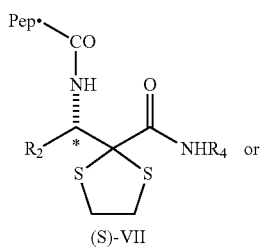

(S)-VII

-continued

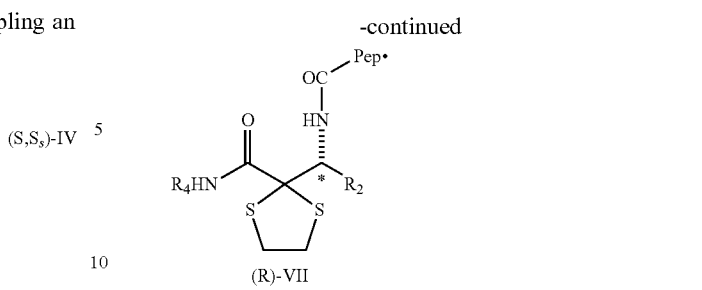

(R)-VII and removing the 1,3-dithiolane protecting group in the compound of Formula (S)-VII or (R)-VII in the presence of an oxidant to provide a peptide of Formula (S)-VIII or (R)-VIII

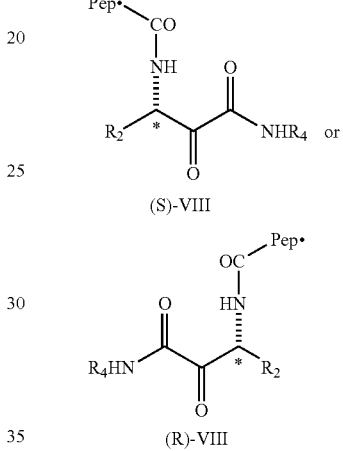

(S)-VIII (R)-VIII containing a β-amino α-keto amide functionality.

In some embodiments, the β-sulfonamide α-keto amide of Formula (S,S$_s$)-IV or (R,R$_s$)-IV

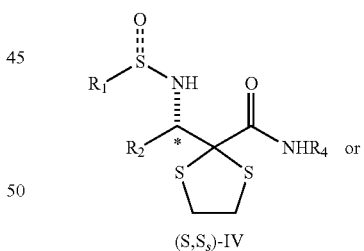

(S,S$_s$)-IV

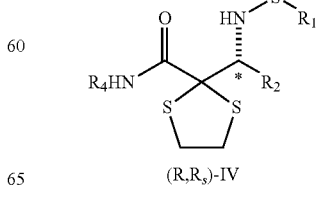

(R,R$_s$)-IV is prepared by a method that includes the steps of:

a) mixing a sulfinimine of Formula ($S_s$)-II or ($R_s$)-II

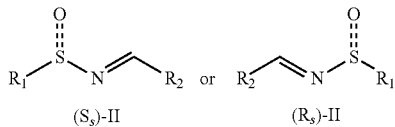

with a dithiolane carboxylate ester of Formula III:

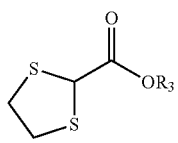

in the presence of a base of sufficient strength to deprotonate the dithiolane hydrogen of Formula III, wherein $R_1$ and $R_2$ in Formula II and $R_3$ in Formula III are as defined above, to give a β-sulfonamide α-keto ester of Formula ($S,S_s$)-I or ($R,R_s$)-I:

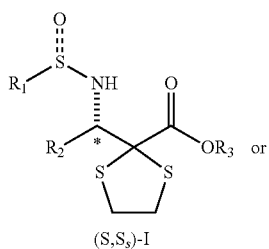

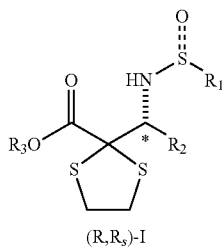

and b) mixing the β-sulfonamide α-keto ester of Formula ($S,S_s$)-I or ($R,R_s$)-I with an amine of the formula $R_4NH_2$, wherein $R_4$ is as defined above, to give a product of Formula ($S,S_s$)-IV or ($R,R_s$)-IV.

Alternatively, the β-sulfonamide α-keto amide of Formula ($S,S_s$)-IV or ($R,R_s$)-IV can be prepared by a method that includes the steps of:

a) mixing a sulfinimine of Formula ($S_s$)-II or ($R_s$)-II

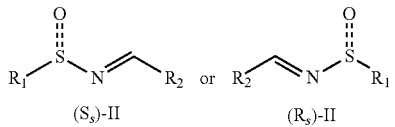

with a dithiolane carboxylate ester of Formula III:

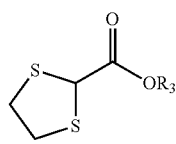

in the presence of a base of sufficient strength to deprotonate the dithiolane hydrogen of Formula III, wherein $R_1$ and $R_2$ in Formula II and $R_3$ in Formula III are as defined above, to give a β-sulfonamide α-keto ester of Formula ($S,S_s$)-I or ($R,R_s$)-I:

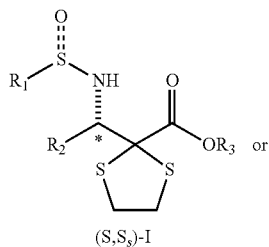

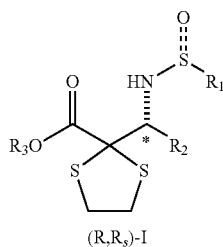

b) mixing the β-sulfonamide α-keto ester of Formula ($S,S_s$)-I or ($R,R_s$)-I with an aqueous base solution optionally in the presence of a co-solvent; neutralizing the solution to provide a carboxylic acid of Formula ($S,S_s$)-V or ($R,R_s$)-V;

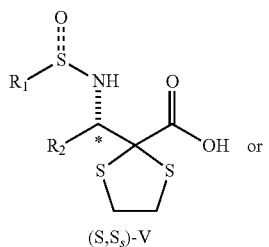

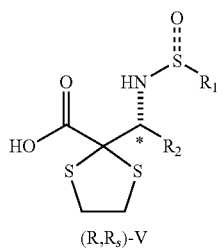

and c) mixing the carboxylic acid of Formula ($S,S_s$)-V or ($R,R_s$)-V with an amine $R_4NH_2$ to provide the β-sulfonamide α-keto amide of Formula ($S,S_s$)-IV or ($R,R_s$)-IV.

Also within the scope of this invention are compounds of Formula I, IV, or VI,

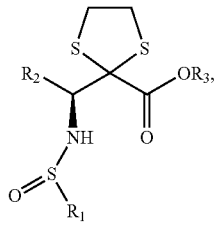

I

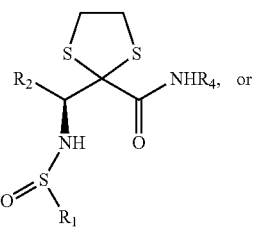

IV

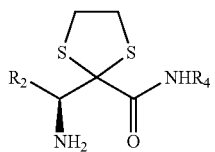

VI wherein each of $R_1$ and $R_3$ independently is alkyl or aryl; and $R_2$ is alkyl, cycloalkyl, (cycloalkyl)alkyl, alkenyl, aryl, or heterocycloalkyl; and $R_4$ is hydrogen, alkyl, cycloalkyl, or aryl.

In some embodiments, $R_1$ is optionally substituted phenyl (e.g., with $C_{1-8}$ or $C_{1-4}$ alkyl). Examples of suitable $R_1$ include, but are not limited to, methylphenyl (e.g., p-methylphenyl, o-methylphenyl, or m-methylphenyl) and ethylphenyl (e.g., p-ethylphenyl, m-ethylphenyl, or o-ethylphenyl).

In some embodiments, $R_1$ is $C_{1-8}$ or $C_{1-4}$ alkyl. Examples of suitable $R_1$ include, but are not limited to, methyl, ethyl, propyl, isopropyl, butyl, and tert-butyl.

In some embodiments, $R_2$ is alkyl (e.g., $C_{1-8}$ or $C_{1-4}$ alkyl), (cycloalkyl)alkyl, or aryl. Examples of suitable $R_2$ include, but are not limited to, methyl, ethyl, propyl, isopropyl, butyl, isobutyl, tert-butyl, (cyclopropyl)methyl, or naphthyl.

In some embodiments, $R_3$ is alkyl (e.g., $C_{1-8}$ or $C_{1-4}$ alkyl). Examples of suitable $R_3$ include, but are not limited to, methyl, ethyl, propyl, isopropyl, and tert-butyl.

In some embodiments, $R_4$ is alkyl or cycloalkyl. Examples of suitable $R_4$ include, but are not limited to, methyl, ethyl, or cyclopropyl.

Specific examples of the compounds of this invention include

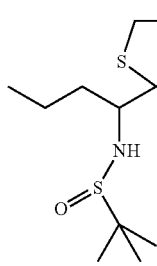 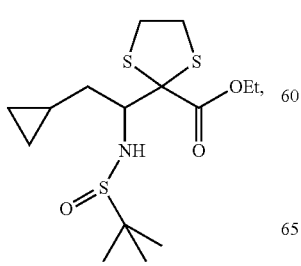

-continued

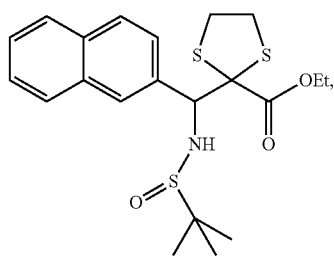

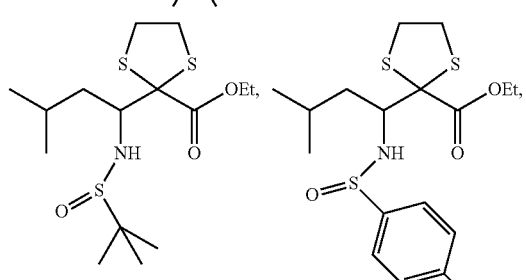

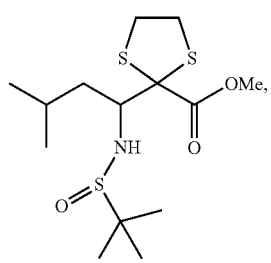

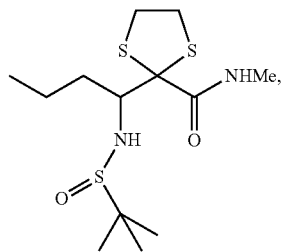

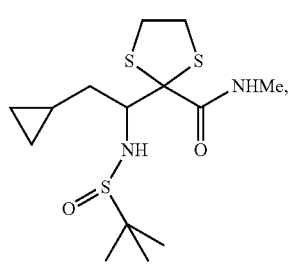

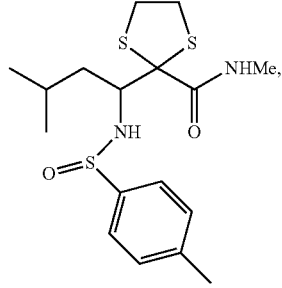

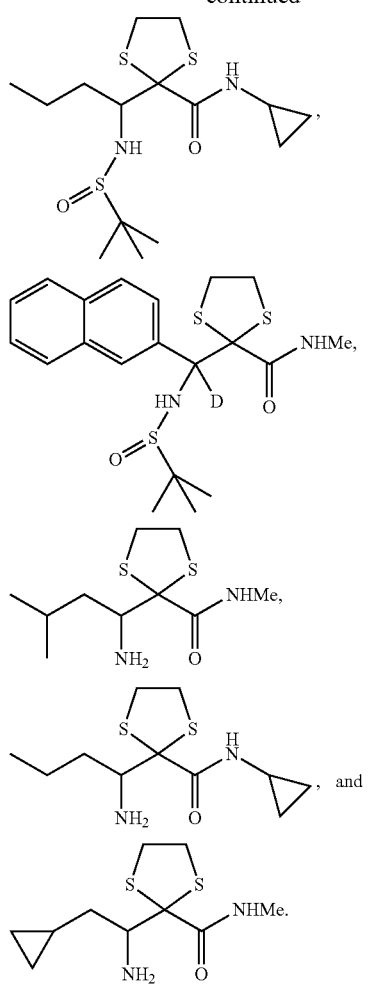
Additional examples of the compounds of this invention include:
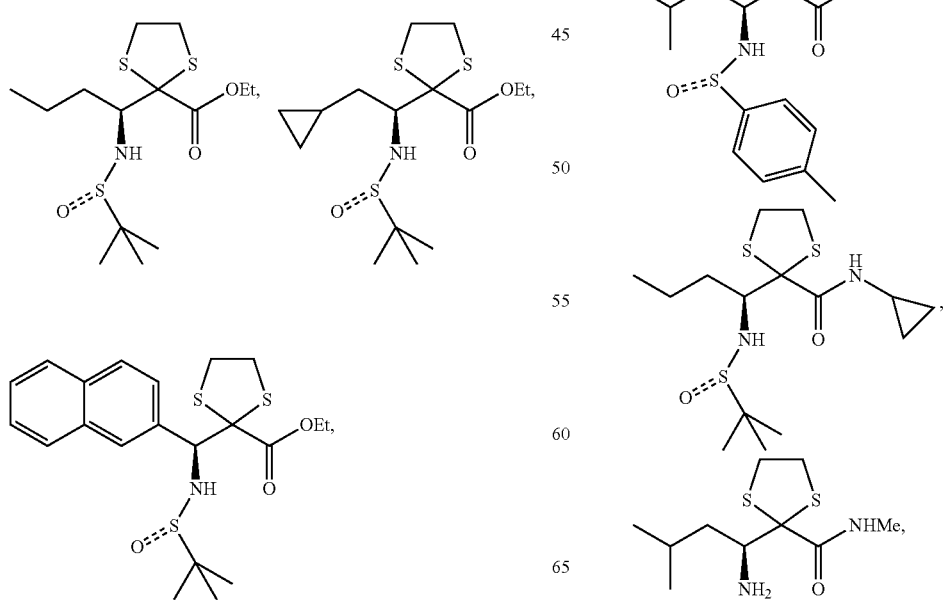

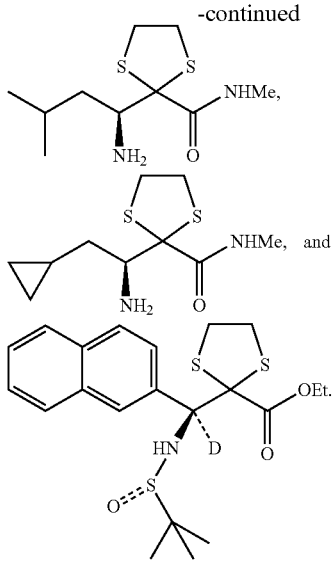

As used herein, the term "enantiomerically pure" means at least 75% (e.g., 85%, 90%, 95%, 99%, or 99.9%) of a designated atom (e.g., carbon or sulfur) center of a compound having the same chirality, i.e., R or S under the Cahn-Ingold-Prelog priority rule. Specifically, if the carbon atom center is oriented so that the lowest-priority of the four is pointed away from a viewer, the viewer will then see two possibilities: If the priority of the remaining three substituents decreases in clockwise direction, it is labeled R (for Rectus), if it decreases in counterclockwise direction, it is S (for Sinister).

Assignment of the R or S configuration to the sulfur atom in sulfinimines and sulfinamides (i.e., S as in

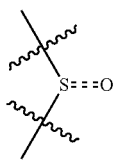

) follows the same principle for tetrahedral carbon atoms. In these compounds, sulfur exhibits tetrahedral coordination wherein one of the four substituents is a lone pair of electrons. This lone pair will invariably be the "small" group (like a hydrogen atom attached to a tetrahedron carbon atom) that is directed away from the viewer toward the back of the molecule when assigning stereochemistry; standard IUPAC priority rules are then applied to the remaining substituents. If in proceeding from the group of highest priority to group of second priority and thence to the third, the eye travels in a clockwise direction, the configuration is specified as R; if counterclockwise, the configuration is specified as S.

In keeping with standard nomenclature, the chirality descriptor with the subscript s in the formula [e.g., $(R_S,R)$-I or $(S,S_s)$-I] refers to the chirality at sulfur while the remaining descriptor refers to the chirality at carbon. Thus, the molecule $(R_S,R)$-I has the (R) absolute configuration at sulfur atom and the (R) absolute configuration at carbon atom. As used herein, the designations of $(R_s,R)$ and $(R,R_s)$ are interchangeable, as are the designations of $(S_s,S)$ and $(S,S_s)$.

As described herein, a specified number range of atoms includes any integer therein. For example, a group having from 1-4 (or 1 to 4) atoms could have 1, 2, 3, or 4 atoms.

As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5$^{th}$ Ed. (Ed.: Smith, M. B. and March, J.), John Wiley & Sons, New York (2001). The entire contents of these two references, as well as other publications cited herein, are hereby incorporated by reference.

As described herein, compounds of the invention may optionally be substituted with one or more substituents, such as are illustrated generally below, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, the term "aliphatic" encompasses linear alkyl, alkenyl, and alkynyl, each of which being optionally substituted as set forth herein. By linear, it is meant that the alkyl, alkenyl, or alkynyl group is not cyclic or the attaching carbon atom of the alkyl, alkenyl, or alkynyl group is not a ring atom.

As used herein, an "alkyl" group refers to a linear saturated aliphatic hydrocarbon group containing 1 to 12 (e.g., 1 to 10, 1 to 8, 1 to 6, or 1 to 4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic (e.g., cycloalkyl or cycloalkenyl), heterocycloaliphatic (e.g., heterocycloalkyl, heterocycloalkenyl, or heterocycloalkynyl), aryl, heteroaryl, alkoxy, aroyl, heteroaroyl, acyl (e.g., (aliphatic)carbonyl, (cycloaliphatic)carbonyl, or (heterocycloaliphatic)carbonyl), nitro, cyano, amido (e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl), amino (e.g., aliphaticamino, cycloaliphaticamino, or heterocycloaliphaticamino), sulfonyl (e.g., aliphatic-SO$_2$—, cycloaliphatic-SO$_2$—, or aryl-SO$_2$—), sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. In some embodiments, the alkyl group can be optionally substituted with halo, cycloaliphatic, aryl, heteroaryl, alkoxy, nitro, cyano, amido, amino, oxo, aryloxy, heteroaryloxy, aralkyloxy, and hydroxyl. In those embodiments, the optional substituents themselves may be further substituted only with one or more of halo, hydroxyl, —NH$_2$, cyano, or nitro. As an example of one embodiment, an alkyl group can be optionally substituted with cycloaliphatic and the cycloaliphatic can, in turn, be substituted with one or more of halo, hydroxyl, —NH$_2$, cyano, or nitro.

Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-SO$_2$-amino)alkyl), aminoalkyl, amidoalkyl, (cycloaliphatic)alkyl, or haloalkyl.

As used herein, an "alkenyl" group refers to a linear aliphatic carbon group that contains 2 to 12 (e.g., 2 to 8, 2 to 6, or 2 to 4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as halo, phospho, cycloaliphatic (e.g., cycloalkyl or cycloalkenyl), heterocycloaliphatic (e.g., heterocycloalkyl or heterocycloalkenyl), aryl, heteroaryl, alkoxy, aroyl, heteroaroyl, acyl (e.g., (aliphatic)carbonyl, (cycloaliphatic)carbonyl, or (heterocycloaliphatic)carbonyl), nitro, cyano, amido (e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl), amino (e.g., aliphaticamino, cycloaliphaticamino, heterocycloaliphaticamino, or aliphaticsulfonylamino), sulfonyl (e.g., aliphatic-SO$_2$—, cycloaliphatic-SO$_2$—, or aryl-SO$_2$—), sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. In some embodiments, the alkenyl group can be optionally substituted with halo, cycloaliphatic, aryl, heteroaryl, alkoxy, nitro, cyano, amido, amino, oxo, aryloxy, heteroaryloxy, aralkyloxy, and hydroxyl. In those embodiments, the optional substituents themselves may be further substituted only with one or more of halo, hydroxyl, —NH$_2$, cyano, or nitro. As an example of one embodiment, an alkenyl group can be optionally substituted with cycloaliphatic and the cycloaliphatic can, in turn, be substituted with one or more of halo, hydroxyl, —NH$_2$, cyano, or nitro.

Without limitation, some examples of substituted alkenyl include cyanoalkenyl, alkoxyalkenyl, acylalkenyl, hydroxyalkenyl, aralkenyl, (alkoxyaryl)alkenyl, (sulfonylamino)alkenyl (such as (alkyl-SO$_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-6 or 2-4) carbon atoms and has at least one triple bond. An alkynyl group can be straight or branched. Examples of suitable alkynyl groups include, but are not limited to, propargyl and butynyl. An alkynyl group can be optionally substituted with one or more substituents such as halo, cycloaliphatic, heterocycloaliphatic, aryl, heteroaryl, alkoxy, aroyl, heteroaroyl, (cycloaliphatic)carbonyl, (heterocycloaliphatic)carbonyl, nitro, cyano, amino, amido, acyl, sulfonyl, sulfinyl, sulfanyl, sulfoxy, urea, thiourea, sulfamoyl, sulfamide, oxo, carboxy, carbamoyl, (cycloaliphatic)oxy, (heterocycloaliphatic)oxy, aryloxy, heteroaryloxy, aralkyloxy, (heteroaryl)alkoxy, or hydroxy. In some embodiments, the alkynyl group can be optionally substituted with halo, cycloaliphatic, aryl, heteroaryl, alkoxy, nitro, cyano, amido, amino, oxo, aryloxy, heteroaryloxy, aralkyloxy, and hydroxyl. In those embodiments, the optional substituents themselves may be further substituted only with one or more of halo, hydroxyl, —NH$_2$, cyano, or nitro. As an example of one embodiment, an alkynyl group can be optionally substituted with cycloaliphatic and the cycloaliphatic can, in turn, be substituted with one or more of halo, hydroxyl, —NH$_2$, cyano, or nitro.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-12 (e.g., 5-12) carbon atoms. Examples of cycloalkyl groups include cyclopropyl, cyclobutyl, cyclopentyl, cyclohexyl, cycloheptyl, adamantyl, norbomyl, cubyl, octahydro-indenyl, decahydro-naphthyl, spiro[5.5]undecanyl, spiro[2.5]octanyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, or ((aminocarbonyl)cycloalkyl)cycloalkyl.

As used herein, a "cycloalkenyl" group refers to a non-aromatic carbocyclic mono- or bicyclic ring of 3 to 12 (e.g., 4 to 8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, spiro[5.5]]undec-3-enyl, spiro[2.5]oct-5-enyl, bicyclo[2.2.2]octenyl, or bicyclo[3.3.1]nonenyl.

A cycloalkyl or cycloalkenyl group can be substituted (i.e., optionally substituted) with one or more substituents such as phosphor; aliphatic (e.g., alkyl, alkenyl, or alkynyl); cycloaliphatic; (cycloaliphatic) aliphatic; heterocycloaliphatic; (heterocycloaliphatic) aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; amido (e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic) aliphatic)carbonylamino, (heteroaryl)carbonylamino, or (heteroaraliphatic)carbonylamino); nitro; carboxy (e.g., HOOC—, alkoxycarbonyl, or alkylcarbonyloxy); acyl (e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl); cyano; halo; hydroxy; mercapto; sulfonyl (e.g., alkyl-SO$_2$— and aryl-SO$_2$—); sulfinyl (e.g., alkyl-S(O)—); sulfanyl (e.g., alkyl-S—); sulfoxy; urea; thiourea; sulfamoyl; sulfamide; oxo; or carbamoyl. In some embodiments, the cycloalkyl or cycloalkenyl group can be each independently and optionally substituted with halo, cycloaliphatic, aryl, heteroaryl, alkoxy, nitro, cyano, amido, amino, oxo, aryloxy, heteroaryloxy, aralkyloxy, and hydroxyl. In those embodiments, the optional substituents themselves may be further substituted only with one or more of halo, hydroxyl, —NH$_2$, cyano, or nitro. As an example of one embodiment, a cycloalkyl group can be optionally substituted with alkoxy and the alkyl portion of the alkoxy can, in turn, be substituted with one or more of halo, hydroxyl, —NH₂, cyano, or nitro.

As used herein, the terms "heterocycle", "heterocyclo", "heterocyclyl", and "heterocyclic" are interchangeable and all refer to non-aromatic, monocyclic, bicyclic, or tricyclic ring systems in which one or more ring members are an independently selected heteroatom. A heterocyclic ring includes heterocycloaliphatic, which in turn includes heterocycloalkyl, heterocycloalkenyl, and heterocycloalkynyl. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Examples of suitable heterocycle for this invention include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 4-piperidinyl, 1-pyrazolinyl, 3-pyrazolinyl, 4-pyrazolinyl, 2-thiazolidinyl, 3-thiazolidinyl, 4-thiazolidinyl, 1-imidazolidinyl, 2-imidazolidinyl, 4-imidazolidinyl, indolinyl, tetrahydroquinolinyl, tetrahydroisoquinolinyl, benzothiolane, benzodithiane, and 1,3-dihydro-imidazol-2-one.

A heterocyclo can be substituted (i.e., optionally substituted), either at the ring carbon atom(s) or the hetero ring atom(s), with one or more substituents such as phosphor; aliphatic (e.g., alkyl, alkenyl, or alkynyl); cycloaliphatic; (cycloaliphatic) aliphatic; heterocycloaliphatic; (heterocycloaliphatic) aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; amido (e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino); nitro; carboxy (e.g., HOOC—, alkoxycarbonyl, or alkylcarbonyloxy); acyl (e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl); cyano; halo; hydroxy; mercapto; sulfonyl (e.g., alkyl-SO₂— and aryl-SO₂—); sulfinyl (e.g., alkyl-S(O)—); sulfanyl (e.g., alkyl-S—); sulfoxy; urea; thiourea; sulfamoyl; sulfamide; oxo; or carbamoyl. In some embodiments, the heterocyclo group can be optionally substituted with halo, cycloaliphatic, aryl, heteroaryl, alkoxy, nitro, cyano, amido, amino, oxo, aryloxy, heteroaryloxy, aralkyloxy, and hydroxyl. In those embodiments, the optional substituents themselves may be further substituted only with one or more of halo, hydroxyl, —NH₂, cyano, or nitro. As an example of one embodiment, a heterocyclo group can be optionally substituted with alkoxy and the alkyl portion of the alkoxy can, in turn, be substituted with one or more of halo, hydroxyl, —NH₂, cyano, or nitro.

Cyclic groups (e.g., cycloaliphatic and heterocycles) can be linearly fused, bridged, or spirocyclic.

The term "heteroatom" or "hetero atom", as used herein, means one or more of oxygen, sulfur, nitrogen, or phosphorus, (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NR⁺ (as in N-substituted pyrrolidinyl)).

The term "unsaturated", as used herein, means that a moiety has one or more units of unsaturation.

The term "nonaromatic", as used herein, describes rings that are either saturated or partially unsaturated.

The term "aromatic", as used herein, describes rings that are fully unsaturated.

The terms "haloalkyl", "haloalkenyl", "haloaliphatic", and "haloalkoxy" mean alkyl, alkenyl, aliphatic, or alkoxy, respectively, substituted with one or more halogen atoms. The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic aromatic ring systems having a total of five to fourteen ring members, wherein at least one ring in the system is aromatic and wherein each ring in the system contains 3 to 7 ring members. The term "aryl" may be used interchangeably with the term "aryl ring." The term "aryl" also refers to heteroaryl ring systems as defined herein below.

An aryl can be optionally substituted with one or more substituents such as phosphor; aliphatic (e.g., alkyl, alkenyl, or alkynyl); cycloaliphatic; (cycloaliphatic) aliphatic; heterocycloaliphatic; (heterocycloaliphatic) aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; amido (e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino); nitro; carboxy (e.g., HOOC—, alkoxycarbonyl, or alkylcarbonyloxy); acyl (e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl); cyano; halo; hydroxy; mercapto; sulfonyl (e.g., alkyl-SO₂— and aryl-SO₂—); sulfinyl (e.g., alkyl-S(O)—); sulfanyl (e.g., alkyl-S—); sulfoxy; urea; thiourea; sulfamoyl; sulfamide; oxo; or carbamoyl. In some embodiments, the aryl group can be optionally substituted with halo, cycloaliphatic, aryl, heteroaryl, alkoxy, nitro, cyano, amido, amino, oxo, aryloxy, heteroaryloxy, aralkyloxy, and hydroxyl. In those embodiments, the optional substituents themselves may be further substituted only with one or more of halo, hydroxyl, —NH₂, cyano, or nitro. As an example of one embodiment, an aryl group can be optionally substituted with alkoxy and the alkyl portion of the alkoxy can, in turn, be substituted with one or more of halo, hydroxyl, —NH₂, cyano, or nitro.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more hetero atoms, and wherein each ring in the system contains 3 to 7 ring members. The term "heteroaryl" may be used interchangeably with the term "heteroaryl ring" or the term "heteroaromatic". Suitable heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

A heteroaryl can be optionally substituted with one or more substituents such as phosphor; aliphatic (e.g., alkyl, alkenyl, or alkynyl); cycloaliphatic; (cycloaliphatic) aliphatic; heterocycloaliphatic; (heterocycloaliphatic) aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; amido (e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino); nitro; carboxy (e.g., HOOC—, alkoxycarbonyl, or alkylcarbonyloxy); acyl (e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl); cyano; halo; hydroxy; mercapto; sulfonyl (e.g., alkyl-SO$_2$— and aryl-SO$_2$—); sulfinyl (e.g., alkyl-S(O)—); sulfanyl (e.g., alkyl-S—); sulfoxy; urea; thiourea; sulfamoyl; sulfamide; oxo; or carbamoyl. In some embodiments, the heteroaryl group can be optionally substituted with halo, cycloaliphatic, aryl, heteroaryl, alkoxy, nitro, cyano, amido, amino, oxo, aryloxy, heteroaryloxy, aralkyloxy, and hydroxyl. In those embodiments, the optional substituents themselves may be further substituted only with one or more of halo, hydroxyl, —NH$_2$, cyano, or nitro. As an example of one embodiment, a heteroaryl group can be optionally substituted with alkoxy and the alkyl portion of the alkoxy can, in turn, be substituted with one or more of halo, hydroxyl, —NH$_2$, cyano, or nitro.

When the term "ortho", "meta", or "para" is used to identify the position of a substituent on a 6-member ring system, it is relative to the atom by which this ring system is attached to the core of the compound of formula. For instance, a phenyl substituted at the ortho-position with methyl, at the meta-position with fluoro, and at the para-position with isopropyl is

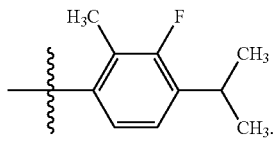

The term "protecting group" and "protective group" as used herein, are interchangeable and refer to an agent used to temporarily block one or more desired reactive sites in a multifunctional compound. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. Exemplary protecting groups are detailed by T. W. Greene et al. in *Protective Groups in Organic Synthesis*, 3$^{rd}$ Edition, John Wiley & Sons, New York (1999) (and other editions of the book), the entire contents of which are incorporated herein by reference. The term "nitrogen protecting group," as used herein, refers to an agents used to temporarily block one or more desired nitrogen reactive sites in a multifunctional compound. Preferred nitrogen protecting groups also possess the characteristics exemplified above, and certain exemplary nitrogen protecting groups are also detailed by T. W. Greene et al. in Chapter 7 of *Protective Groups in Organic Synthesis*, 3$^{rd}$ Edition.

In some embodiments, an alkyl or aliphatic chain can be optionally interrupted with another atom or group. This means that a methylene unit of the alkyl or aliphatic chain is optionally replaced with said other atom or group. Examples of such atoms or groups would include, but are not limited to, —NR—, —O—, —S—, —CO$_2$—, —OC(O)—, —C(O)CO—, —C(O)—, —C(O)NR—, —C(=N—CN)—, —NRCO—, —NRC(O)O—, —SO$_2$NR—, —NRSO$_2$—, —NRC(O)NR—, —OC(O)NR—, —NRSO$_2$NR—, —SO—, or —SO$_2$—, wherein R is defined herein. Unless otherwise specified, the optional replacements form a chemically stable compound. Optional interruptions can occur both within the chain and at either end of the chain; i.e., both at the point of attachment and/or also at the terminal end. Two optional replacements can also be adjacent to each other within a chain so long as it results in a chemically stable compound. The optional interruptions or replacements can also completely replace all of the carbon atoms in a chain. For example, a C$_3$ aliphatic can be optionally interrupted or replaced by —NR—, —C(O)—, and —NR— to form —NRC(O)NR— (i.e., a urea). In some embodiments, an alkyl or aliphatic chain is not interrupted, and none of the carbon units is replaced, with any of the hetero atoms or groups identified above.

Unless otherwise specified, if the replacement or interruption occurs at the terminal end, the replacement atom is bound to an H on the terminal end. For example, if —CH$_2$CH$_2$CH$_3$ were optionally interrupted with —O—, the resulting compound could be —OCH$_2$CH$_3$, —CH$_2$OCH$_3$, or —CH$_2$CH$_2$OH.

As used herein, the term "mineral acid" refers to an acid derived by chemical reaction from inorganic minerals, as opposed to organic acids. In these acids, at least a hydrogen atom is covalently bonded with an anion, such as sulfate or chloride. Examples of mineral acids include hydrochloric acid, nitric acid, phosphoric acid, sulfuric acid, boric acid, and hydrofluoric acid.

As used herein, the term "coupling agent" refers to a compound that helps or accelerates the reaction between two other molecules and forming a new molecule. Examples of coupling agents that can be used for this invention include dicyclohexylcarbodiimide (DCC), diisopropylcarbodiimide (DIC), di-p-toluoylcarbodiimide, 1-benzotriazole diethylphosphate-1-cyclohexyl-3-(2-morpholinylethyl)carbodiimide (BDP), 1-(3-dimethylaminopropyl)-3-ethyl-carbodiimide hydrochloride (EDC), cyanuric fluoride, cyanuric chloride, tetramethyl fluoroformamidinium hexafluorophosphate (TFFH), diphenylphosphorazidate (DPPA), benzotriazol-1-yloxytris(dimethylamino)phosphonium hexafluorophosphate (BOP), O-benzotriazol-1-yl-N,N,N', N1-tetramethyluronium hexafluorophosphate (HBTU), P-benzotriazol-1-yl-N,N,N'N1-tetramethyluronium tetrafluoroborate (TBTU), N-[(dimethylamino)-1-H-1,2,3-triazolo[4,5,6]-pyridin-1-ylmethylene]-N-methylmethanaminium hexafluorophosphate N-oxide (HATU), bis(2-oxo-3-oxazolidinyl)phosphinic chloride (BOP-C1), (1-H-1,2,3-benzotriazol-1-yloxy)-tris(pyrrolidino)phosphonium tetrafluorophopsphate (PyBOP), bromotris(dimethylamino) phosphonium hexafluorophosphate (BrOP), 3-(diethoxy-phosphoryloxy)-1,2,3-benzotriazin-4(3H)-one (DEPBT), or (bromotris(pyrrolidoino)phosphonium hexafluorophosphate (PyBrOP). The amount of peptide coupling reagent used for the methods of this invention can range, e.g., from about 1.0 to about 10.0 equivalents. Optional reagents that may be used in the amide bond-forming reaction include 4-dimethylaminopyridine (DMAP) or active ester reagents, such as 1-hydroxybenzotriazole (HOB T), hydroxyazabenzotriazole (HOAT), hydroxysuccinimide (HOSu), endo-N-hydroxy-5-norbornene-2,3-dicarboxamide (HONB), in amounts ranging from about 1.0 to about 10.0 equivalents.

As used herein, the term "oxidant" or "oxidizing agent" refers to a chemical compound that readily transfers oxygen atoms, or a substance that gains electrons in a redox chemical reaction. Examples of oxidants that can be used for this invention include N-bromosuccinimide, 1,3-dibromo-5,5-dimethylhydantoin, bromine, iodine, 3-chloroperoxybenzoic acid, or hydrogen peroxide in combination with a transition metal catalyst (e.g., a compound containing titanium, vanadium, molybdenum, or rhenium). Additional examples of suitable oxidants are provided by A. K. Banerjee et al. in *Russian Chemical Reviews,* 69, 947-955 (2000), the entire contents of which, as well as other publications cited therein, are incorporated herein by reference.

As used herein, the term "peptide" or "peptidyl compound" refers to a compound comprising at least one amino acid (i.e., including a single amino acid or a peptide of at least 2 amino acids (e.g., from 2 to 24 amino acids or from 2 to 18 amino acids)) that can be coupled with a β-amino α-keto ester, acid, or amide of this invention. The amino acid, either alone or as a unit of a peptide having at least two amino acids, can be natural or non-natural, as those known by a skilled person in the art. See, e.g., G. Zubay, *Biochemistry,* 3$^{rd}$ Ed., Wm. C. Brown Publishers, 1993.

As used herein, the term "mixing" a compound with another compound means adding a compound (or its solution) to another compound (or its solution) so to allow the two compounds to undergo a chemical reaction, either substantially (e.g., at least 50%) or completely, and give rise to a new product.

Unless otherwise stated or exemplified, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention.

Unless otherwise stated, a substituent can freely rotate around any rotatable bonds. For example, a substituent drawn as

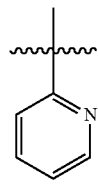

also represents

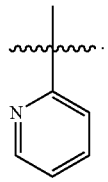

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

As used herein, a suitable "base" or "a base of sufficient strength to deprotonate the dithiolane hydrogen of Formula III" refers to a base that is strong enough to remove, either completely or substantially (e.g., at least 75%, such as 85 or 95%), the hydrogen atom bonded to the carbon atom between the two sulfur atoms in the compound of Formula III (i.e., the circled hydrogen in

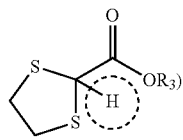

so that the deprotonated compound can react with the compound of Formula II. Suitable strong bases for use in this invention include alkali metal bases for which the conjugate acid has a pKa higher than about 16. Examples of suitable bases include, but are not limited to, lithium hexamethyldisilamide, hexynyllithium, lithium diisoproplyamide, sodium hexamethyldisilamide, sodium hydride, potassium hexamethyldisilamide, potassium hydride, potassium tert-butoxide, and potassium tert-amyloxide. Alternatively, the base may be generated in situ by the action of an alkali metal hydride on a conjugate acid with pKa higher than about 16 such as an alcohol or dialkylamine.

Suitable solvents for this invention include protic and aprotic solvents provided that the pK$_a$ of any protic solvent is not lower than about 16. Examples of such solvents include, but are not limited to, dimethoxyethane, tert-butyl alcohol, methyl tert-butyl ether, dimethylformamide, and tetrahydrofuran.

The process of the instant invention is readily carried out as described below. Solvents, temperatures, and other reaction conditions may readily be selected by one of ordinary skill in the art. Starting materials are commercially available or can be readily prepared by one of ordinary skill in the art.

In accordance with the process of the present invention an enantiomerically pure sulfinimine of Formula II is treated with a dithiolanecarboxylate ester of Formula III in the presence of a strong base. The molar ratio of the sulfinimine II to dithiocarboxylate ester III is between 0.8:1 and 1.2:1, preferably between 0.9:1 and 1.1:1.

The reaction of compounds III and IV with the base may be carried out at a temperature range of about −80° C. to about 0° C. A reaction temperature within the range from about −80°

C. to about −35° C. is preferred and most preferred is a reaction temperature with a range from about −35 to about −45°.

The starting materials for the process of preparing protected beta-amino alpha-keto esters of Formula (I) in accordance with the present invention are an alkyl dithiolanecarboxylate ester of Formula (III) and an enantiomerically pure sulfinimine of Formula (II). Alkyl dithiolanecarboxylate esters of Formula (III) are commercially available or are readily prepared by methods known to one of ordinary skill in the art. Enantiomerically pure sulfinimines are prepared by the condensation of an aldehyde with an enantiomerically pure sulfinamide, both of which are commercially available. Detailed procedures for such condensations are described by Liu et al. in the *Journal of Organic Chemistry*, 64, 1278-1284 (1999), the entire contents of which are incorporated herein by reference.

The methods of this invention can be used to prepare β-amino α-keto esters or amides which may have medicinal activities in themselves or can be used as intermediates for synthesizing peptidyl compounds that have pharmaceutical applications such as, e.g., viral protease inhibitors for the treatment of HIV and hepatitis C. Uses of compounds for such treatment are readily available to a skilled person to which this invention relates. See, e.g., WO 98/17679, WO 99/50230, WO 01/74768, WO 02/018369, WO 03/006490, WO 03/035060, WO 03/087092, WO 04/092161, WO 04/092162, WO 05/077965, WO 05/037860, WO 05/007681, WO 05/035535, WO 05/028502, WO 05/090334, WO 07/025307, WO 07/016589, WO 07/098270, WO 07/142951, WO 07/109080, WO 07/109023. PCT/US2008/02541 (filed Feb. 27, 2008, titled "INHIBITORS OF SERINE PROTEASES"), PCT/US2008/02395 (filed Feb. 21, 2008, titled "INHIBITORS OF SERINE PROTEASES"), PCT/US2008/02568 (filed Feb. 27, 2008, titled "CO-CRYSTALS AND PHARMACEUTICALS COMPOSITIONS COMPRISING THE SAME"), and U.S. 60/696,012 (filed Aug. 30, 2007 titled "CO-CRYSTALS AND PHARMACEUTICAL COMPOSITIONS COMPRISING THE SAME"). The contents of these publications or applications are incorporated herein by reference in their entireties.

The following schemes include reactions for the methods of this invention, without showing the steric configurations of any of the reactants or products.

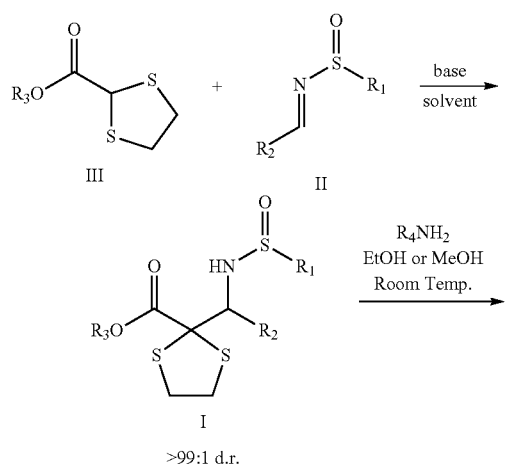

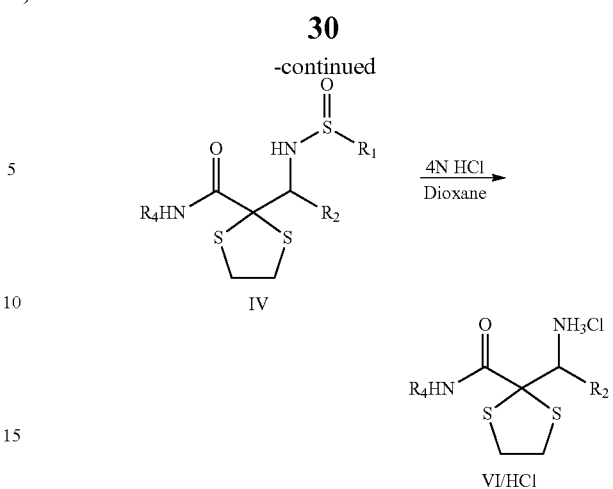

Set forth below are specific examples of the methods and compounds of this invention. They are intended to be only illustrative and not in any way limiting.

EXAMPLE 1

Preparation of Ethyl (S,S$_S$)-2-(1-tert-butylsulfinylamino)butyl-1,3-dithiolanecarboxylate

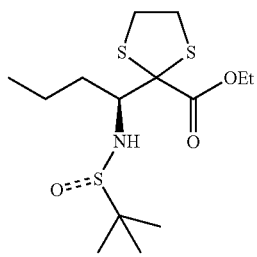

Method 1: Lithium Bis(trimethylsilyl)amide in THF

A flask was charged with a solution of ethyl 1,3-dithiolanecarboxylate (2.00 g, 11.2 mmol) and [N(E),S(S)]-2-methyl-N-(butylidene)-2-propanesulfinamide (2.17 g, 90% purity, 11.2 mmol) in tetrahydrofuran (THF, 33 mL) under a nitrogen atmosphere. The solution was cooled to −78° C. whereupon a 1.0 M solution of lithium bis(trimethylsilyl)amide (13.6 mL, 13.6 mmol) in THF was added dropwise. The mixture was stirred for 2 hours at −78° C. and was then added to half-saturated aqueous ammonium chloride (100 mL) and the product was extracted into ethyl acetate (twice, 50 mL each). After drying over sodium sulfate, the solvent was distilled at reduced pressure and dried in high vacuum to afford the title compound as yellow oil (3.66 g, 92%). HPLC analysis and NMR revealed the product was a single diastereomer.

$^1$H-NMR (500 MHz, CDCl$_3$): δ 0.82 (t, J=7 Hz, 3H), 1.19 (s, 9H), 1.23 (t, J=7, 3H), 1.23-1.58 (m, 4H), 3.22-3.42 (m, 4H), 3.70 (m, 1H), 3.81 (m, 1H), 4.19 (q, J=7 Hz, 2H).

$^{13}$C-NMR (125 MHz, CDCl$_3$): δ 13.5, 13.9, 20.0, 22.1, 37.8, 39.95, 39.98, 56.9, 61.7, 62.3, 76.24, 171.00.

Method 2: Lithium Bis(trimethylsilyl)amide in MTBE

A flask was charged with a solution of ethyl 1,3-dithiolanecarboxylate (0.36 g, 2.0 mmol) and [N(E),S(S)]-2-methyl- N-(butylidene)-2-propanesulfinamide (0.38 g, 90% purity, 2.0 mmol) in methyl tert-butyl ether (5.0 mL) under a nitrogen atmosphere. The solution was cooled to −78° C. whereupon a 1.0 M solution of lithium bis(trimethylsilyl)amide (2.4 mL, 2.4 mmol) in MTBE was added dropwise. The mixture was stirred for 2 hours at −78° C. and was then added to half-saturated aqueous ammonium chloride (50 mL) and the product was extracted into ethyl acetate (twice, 25 mL each). After drying over sodium sulfate, the solvent was distilled at reduced pressure and dried in high vacuum to afford ethyl $(S,S_S)$-2-[1-tert-butylsulfinylamino)butyl-1,3-dithiolanecarboxylate as yellow oil (0.72 g, 100%). HPLC analysis indicated that conversion was 100% and NMR spectral data were essentially identical to those in Method 1.

Method 3: Lithium Bis(trimethylsilyl)amide in Toluene

A flask was charged with a solution of ethyl 1,3-dithiolanecarboxylate (0.36 g, 2.0 mmol) and [N(E),S(S)]-2-methyl-N-(butylidene)-2-propanesulfinamide (0.38 g, 90% purity, 2.0 mmol) in toluene (5.0 mL) under a nitrogen atmosphere. The solution was cooled to −78° C. whereupon a 1.0 M solution of lithium bis(trimethylsilyl)amide (2.4 mL, 2.4 mmol) in toluene was added dropwise. The mixture was stirred for 2 hours at −78° C. and was then added to half-saturated aqueous ammonium chloride (50 mL) and the product was extracted into ethyl acetate (twice, 25 mL each). After drying over sodium sulfate, the solvent was distilled at reduced pressure and dried in high vacuum to afford 0.69 g of oily residue. HPLC analysis indicated that conversion is 42%. NMR spectral data were consistent with those for the product of Method 1 in addition to 58% of recovered starting materials.

Method 4: Hexynyllithium in Hexane

A solution of hexynyllithium was prepared by dropwise addition of a 1.6 M solution of butyl lithium (1.51 mL, 2.42 mmol) in hexanes to a solution of 1-hexyne (0.25 g, 3.0 mmol) in THF (5.0 mL).

A flask was charged with a solution of ethyl 1,3-dithiolanecarboxylate (0.36 g, 2.0 mmol) and [N(E),S(S)]-2-methyl-N-(butylidene)-2-propanesulfinamide (0.38 g, 90% purity, 2.0 mmol) in THF (5.0 mL) under a nitrogen atmosphere. The solution was cooled to −78° C. and the hexynyllithium solution was added dropwise. The mixture was stirred for 2 hours at −78° C. and was then added to half-saturated aqueous ammonium chloride (50 mL) and the product was extracted into ethyl acetate (twice, 25 mL each time). After drying over sodium sulfate, the solvent was distilled at reduced pressure and dried in high vacuum to afford ethyl $(S,S_S)$-2-[1-tert-butylsulfinylamino)butyl-1,3-dithiolanecarboxylate as yellow oil (0.69 g, 97%). HPLC analysis indicated that conversion was 100% and NMR spectral data were essentially identical to those in Method 1.

Method 5: Lithium Diisopropylamide in Hexane

A solution of lithium diisopropylamide was prepared by dropwise addition of a 1.6 M solution of butyl lithium (1.51 mL, 2.42 mmol) in hexanes to a solution of diisopropylamine (400 µL, 2.8 mmol) in THF (5.0 mL).

A flask was charged with a solution of ethyl 1,3-dithiolanecarboxylate (0.36 g, 2.0 mmol) and [N(E),S(S)]-2-methyl-N-(butylidene)-2-propanesulfinamide (0.38 g, 90% purity, 2.0 mmol) in THF (5.0 mL) under a nitrogen atmosphere. The solution was cooled to −78° C. and the lithium diisopropylamide solution was added dropwise. The mixture was stirred for 2 hours at −78° C. and was then added to half-saturated aqueous ammonium chloride (50 mL) and the product was extracted into ethyl acetate (twice, 25 mL each time). After drying over sodium sulfate, the solvent was distilled at reduced pressure and dried in high vacuum to afford ethyl $(S,S_S)$-2-[1-tert-butylsulfinylamino)butyl-1,3-dithiolanecarboxylate as yellow oil (0.72 g, 100%). HPLC analysis indicated that conversion was greater than 95% and NMR spectral data were essentially identical to those in Method 1.

Method 6: Sodium Bis(trimethylsilyl)amide in THF

A flask was charged with a solution of ethyl 1,3-dithiolanecarboxylate (0.36 g, 2.0 mmol) and [N(E),S(S)]-2-methyl-N-(butylidene)-2-propanesulfinamide (0.38 g, 90% purity, 2.0 mmol) in THF (5.0 mL) under a nitrogen atmosphere. The solution was cooled to −78° C. whereupon a 1.0 M solution of sodium bis(trimethylsilyl)amide (2.4 mL, 2.4 mmol) in THF was added dropwise. The mixture was stirred for 2 hours at −78° C. and was then added to half-saturated aqueous ammonium chloride (50 mL) and the product was extracted into ethyl acetate (twice, 25 mL each time). After drying over sodium sulfate, the solvent was distilled at reduced pressure and dried in high vacuum to afford ethyl $(S,S_S)$-2-[1-tert-butylsulfinylamino)butyl-1,3-dithiolanecarboxylate as yellow oil (0.68 g, 96%). HPLC analysis indicated that conversion is 100% and NMR spectral data were essentially identical to those in Method 1.

Method 7: Potassium Bis(trimethylsilyl)amide in Mixed Solvent

A flask was charged with a solution of ethyl 1,3-dithiolanecarboxylate (0.36 g, 2.0 mmol) and [N(E),S(S)]-2-methyl-N-(butylidene)-2-propanesulfinamide (0.38 g, 90% purity, 2.0 mmol) in THF (5.0 mL) under a nitrogen atmosphere. The solution was cooled to −78° C. whereupon a 1.0 M solution of potassium bis(trimethylsilyl)amide (2.4 mL, 2.4 mmol) in toluene was added dropwise. The mixture was stirred for 2 hours at −78° C. and was then added to half-saturated aqueous ammonium chloride (50 mL) and the product was extracted into ethyl acetate (twice, 25 mL each time). After drying over sodium sulfate, the solvent was distilled at reduced pressure and dried in high vacuum to afford 0.69 g of oily residue. HPLC analysis indicated that conversion is 71%. NMR spectral data were consistent with those for the product of Method 1 in addition to 29% of recovered starting materials.

COMPARATIVE EXAMPLE

Ethyl Dithianecarboxylate

A flask was charged with a solution of ethyl 1,3-dithianecarboxylate (0.38 g, 2.0 mmol) and [N(E),S(S)]-2-methyl-N-(3-methylbutylidene)-2-propanesulfinamide (0.41 g, 90% purity, 2.0 mmol) in tetrahydrofuran (5.0 mL) under a nitrogen atmosphere. The solution was cooled to −78° C. whereupon a 1.0 M solution of lithium bis(trimethylsilyl)amide in THF (2.4 mL, 2.4 mmol) was added dropwise. The mixture was stirred for 2 hours at −78° C. and was then added to half-saturated aqueous ammonium chloride (50 mL) and the product was extracted into ethyl acetate (twice, 25 mL each time). After drying over sodium sulfate, the solvent was distilled at reduced pressure and dried in high vacuum to afford 0.67 g of oily residue. HPLC and NMR analysis showed the presence of ethyl (S,S$_S$)-2-[1-tert-butylsulfinylylamino)-3-methylbutyl-1,3-dithianecarboxylate as a single diastereomer but indicated that the conversion of the reaction was limited to 42%.

In a separate experiment, a flask was charged with a solution of ethyl 1,3-dithianecarboxylate (0.38 g, 2.0 mmol) and [N(E),S(S)]-2-methyl-N-(butylidene)-2-propanesulfinamide (0.38 g, 90% purity, 2.0 mmol) in tetrahydrofuran (5.0 mL) under a nitrogen atmosphere. The solution was cooled to −78° C. whereupon a 1.0 M solution of lithium bis(trimethylsilyl)amide (2.4 mL, 2.4 mmol) in THF was added dropwise. The temperature was allowed to rise to −20° C. over the course of 2 hours. The mixture was then added to half-saturated aqueous ammonium chloride (50 mL) and the product was extracted into ethyl acetate (twice, 25 mL each time). After drying over sodium sulfate, the solvent was distilled at reduced pressure and dried in high vacuum to afford 0.59 g of oily residue. HPLC and NMR analysis showed that 45% conversion to ethyl 2-[1-tert-butylsulfinylamino)butyl-1,3-dithiolanecarboxylate had occurred but that the material was a nearly 1:1 mixture of the (S,S$_S$) and (R,S$_S$) diastereomers.

EXAMPLE 2

Preparation of Ethyl (S,S$_s$)-2-[1-tert-butylsulfinylamino)-2-cyclopropylethyl]-1,3-dithiolane-2-carboxylate

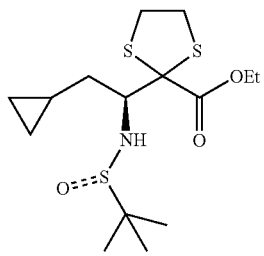

Ethyl 1,3-dithiolane-2-carboxylate (1.58 g, 8.70 mmol) was added to a filtered solution of [N(E),S(S)]-2-methyl-N-(2-cyclopropylethylidene)-2-propanesulfinamide (1.63 g, 8.70 mmol) in 2-methyltetrahydrofuran (15.5 mL). The solution was cooled to −78° C. and a 1.0 M solution of lithium bis(trimethylsilyl)amide in THF (11.0 mL, 11.0 mmol) was added via syringe pump at a rate of 1 mL/min. The mixture was stirred for an additional 2 hours at −76 to −65° C. at which time HPLC analysis indicated the reaction was complete. Acetic acid (742 µL, 13.0 mmol) was added in one portion and the mixture was allowed to warm. Water (10 mL) was added and the product was extracted into isopropyl acetate (three times, 10 mL each time). The combined organics were dried over sodium sulfate, concentrated at reduced pressure, and dried overnight at 2.7 torr to afford ethyl 2-[(1S)-1-tert-butylsulfinylamino)-2-cyclopropylethyl]-1,3-dithiolane-2-carboxylate (1.64 g, 83%) as an amber oil.

$^1$H-NMR (500 MHz, DMSO-d$_6$): δ 5.05 (d, J=12.7 Hz, 1H), 4.14-4.07 (m, 2H), 3.82 (t, J=7.2 Hz, 1H), 3.44-3.36 (m, 3H), 3.30-3.19 (m, 2H), 1.21-1.16 (m, 3H), 1.11 (s, 9H), 0.98-0.94 (m, 2H), 0.48-0.36 (m, 1H), 0.35-0.30 (m, 1H), 0.11-0.08 (m, 1H), 0.036-0.09 (m, 1H).

$^{13}$C-NMR (125 MHz, DMSO-d$_6$): δ 168.6, 74.5, 60.8, 60.0, 54.3, 48.6, 36.5, 36.3, 20.8, 12.0, 7.2, 3.9, 2.5.

EXAMPLE 3

Preparation of Ethyl (S,S$_s$)-2-[(tert-butylsulfinylamino)-(2-naphthyl)methyl]-1,3-dithiolane-2-carboyxlate

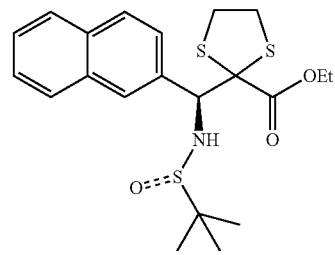

A flask was charged with ethyl 1,3-dithiolane-2-carboxylate (0.36 g, 2.0 mmol) and [N(E),S(S)]-2-methyl-N-(2-naphthylmethylene)propane-2-sulfinamide (0.52 g, 2.0 mmol) in tetrahydrofuran (5.0 mL) under a nitrogen atmosphere. The solution was cooled to −78° C. whereupon a 1.0 M solution of lithium bis(trimethylsilyl)amide in THF (2.4 mL, 2.4 mmol) was added dropwise. The mixture was stirred for 2 hours at −78° C. and was then added to half-saturated aqueous ammonium chloride (50 mL) and the product was extracted into ethyl acetate (twice, 25 mL each time). After drying over sodium sulfate, the solvent was removed at reduced pressure. HPLC and NMR analyses indicated that the reaction was 85% compete. The crude product was purified by flash chromatography, eluting with 2:1 ethyl acetate/hexanes. Distillation of solvent afforded ethyl 2-(S)-[(tert-butylsulfinylamino)-(2-naphthyl)methyl]-1,3-dithiolane-2-carboyxlate (0.68 g, 78%) as a colorless oil.

$^1$H-NMR (500 MHz, CDCl$_3$): δ 1.10 (s, 9H), 1.12 (t, J=7.3, 3H), 3.14-3.27 (m, 4H), 4.04 (m, 2H), 4.52 (d, J=5.4 Hz, 1H), 5.19 (d, J=5.4 Hz, 1H), 7.36-7.41 (m, 2H), 7.49 (m, 1H), 7.68-7.74 (m, 3H), 7.79 (s, 1H).

$^{13}$C-NMR (125 MHz, CDCl$_3$): δ 13.9, 22.5, 40.1, 40.4, 56.3, 62.8, 63.7, 77.0, 126.17, 126.24, 126.4, 127.6, 127.8, 128.2, 128.9, 132.8, 133.5, 135.0, 170.2.

EXAMPLE 4

Preparation of Ethyl (S,S$_S$)-2-[1-tert-butylsulfinylamino)-3-methylbutyl-1,3-dithiolanecarboxylate

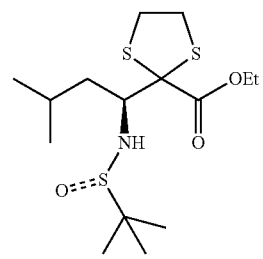

Method 1: Lithium Bis(trimethylsilyl)amide in THF

A flask was charged with a solution of ethyl 1,3-dithiolanecarboxylate (1.62 g, 9.09 mmol) and [N(E),S(S)]-2-methyl-N-(3-methylbutylidene)-2-propanesulfinamide (1.90 g, 90% purity, 9.04 mmol) in tetrahydrofuran (27 mL) under a nitrogen atmosphere. The solution was cooled to −78° C. whereupon a 1.0 M solution of lithium bis(trimethylsilyl)amide in THF (11.0 mL, 11.0 mmol) was added dropwise. The mixture was stirred for 2 hours at −78° C. and was then added to half-saturated aqueous ammonium chloride (100 mL) and the product was extracted into ethyl acetate (twice, 50 mL each time). After drying over sodium sulfate, the solvent was distilled at reduced pressure and dried in high vacuum to afford ethyl (S,$S_S$)-2-[1-tert-butylsulfinylamino)-3-methylbutyl-1,3-dithiolanecarboxylate as yellow oil (3.17 g, 95%). HPLC analysis and NMR revealed the product to consist of a single diastereomer.

$^1$H-NMR ($C_6D_6$): δ 0.72 (d, J=7, 3H), 0.79 (d, J=7 Hz, 3H), 0.89 (t, J=7 Hz, 3H), 0.98 (s, 9H), 1.28 (m, 1H), 1.50 (m, 1H), 1.81 (m, 1H), 3.80-3.94 (m, 3H), 3.15 (m, 1H), 3.75 (m, 1H), 3.92 (q, J=7, 2H), 4.07 (m, 1H).

$^{13}$C-NMR ($C_6D_6$): δ 12.0, 19.1, 20.7, 22.0, 23.2, 38.3, 38.4, 43.3, 54.7, 58.9, 60.3, 75.3, 169.2.

Method 2: Potassium tert-Butoxide in THF

A flask was charged with a solution of ethyl 1,3-dithiolanecarboxylate (0.36 g, 2.00 mmol) and [N(E),S(S)]-2-methyl-N-(3-methylbutylidene)-2-propanesulfinamide (0.42 g, 90% purity, 2.00 mmol) in tetrahydrofuran (27 mL) under a nitrogen atmosphere. The solution was cooled to −78° C. whereupon a 1.0 M solution of potassium tert-butoxide in THF (2.4 mL, 2.4 mmol) was added dropwise. The mixture was stirred for 2 hours at −78° C. and was then added to half-saturated aqueous ammonium chloride (50 mL) and the product was extracted into ethyl acetate (twice, 25 mL each time). After drying over sodium sulfate, the solvent was distilled at reduced pressure and dried in high vacuum to afford ethyl (S,$S_S$)-2-[1-tert-butylsulfinylylamino)-3-methylbutyl-1,3-dithiolanecarboxylate as yellow oil (0.71 g, 96%). HPLC analysis and NMR indicated the product is essentially identical to that produced in Method 1.

EXAMPLE 5

Preparation of Ethyl (S,$S_S$)-2-[4-methylphenylsulfinylamino)-3-methylbutyl-1,3-dithiolanecarboxylate

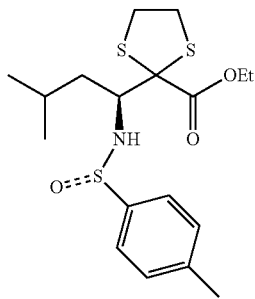

A flask was charged with a solution of ethyl 1,3-dithiolanecarboxylate (0.36 g, 2.0 mmol) and [N(E),S(S)]-4-methyl-N-(3-methylbutylidene)-2-phenylsulfinamide (0.50 g, 90% purity, 2.0 mmol) in tetrahydrofuran (5.0 mL) under a nitrogen atmosphere. The solution was cooled to −78° C. whereupon a 1.0 M solution of lithium bis(trimethylsilyl)amide (2.4 mL, 2.4 mmol) was added dropwise. The mixture was stirred for 2 hours at −78° C. and was then added to half-saturated aqueous ammonium chloride (50 mL) and the product was extracted into ethyl acetate (twice, 25 mL each time). After drying over sodium sulfate, the solvent was distilled at reduced pressure and dried in high vacuum to afford ethyl (S,$S_S$)-2-[4-methylphenylsulfinylamino)-3-methylbutyl-1,3-dithiolanecarboxylate as yellow oil (0.81 g, 100%). HPLC analysis indicated that the product consisted of 2 diastereomers in a 98:2 ratio.

$^1$H-NMR (500 MHz, $CDCl_3$) for the major diastereomer: δ 0.80 (d, J=6.5 Hz, 3H), 0.85 (d, J=6.5 Hz, 3H), 1.17 (td, J=7.1, 1.9 Hz, 3H), 1.41 (m, 1H), 1.79 (m, 1H), 2.14-2.25 (m, 1H), 2.27 (s, 3H), 3.15-3.34 (m, 4H), 3.93-4.04 (m, 1H), 4.11 (q, J=7.1 Hz, 2H), 4.36 (d, J=9.7 Hz, 1H), 7.16 (d, J=8.1 Hz, 2H), 7.49 (d, J=8.1 Hz, 2H).

$^{13}$C-NMR (125 MHz, $CDCl_3$): δ 13.9, 20.9, 21.3, 23.8, 24.9, 39.99, 40.02, 44.7, 60.9, 62.5, 76.1, 125.3, 129.3, 141.2, 144.0, 171.0.

EXAMPLE 6

Preparation of Methyl (S,$S_S$)-2-[1-tert-butylsulfinylylamino)-3-methylbutyl-1,3-dithiolanecarboxylate

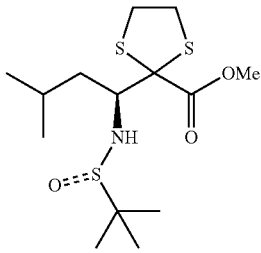

A flask was charged with a solution of methyl 1,3-dithiolanecarboxylate (0.33 g, 2.00 mmol) and [N(E),S(S)]-2-methyl-N-(3-methylbutylidene)-2-propanesulfinamide (0.42 g, 90% purity, 2.00 mmol) in tetrahydrofuran (5.0 mL) under a nitrogen atmosphere. The solution was cooled to −78° C. whereupon a 1.0 M solution of lithium bis(trimethylsilyl)amide (2.4 mL, 2.4 mmol) was added dropwise. The mixture was stirred for 2 hours at −78° C. and was then added to half-saturated aqueous ammonium chloride (50 mL) and the product was extracted into ethyl acetate (twice, 25 mL each time). After drying over sodium sulfate, the solvent was distilled at reduced pressure and dried in high vacuum to afford methyl (S,$S_S$)-2-[1-tert-butylsulfinylylamino)-3-methylbutyl-1,3-dithiolanecarboxylate as a yellow oil (0.69 g, 97%). HPLC analysis and NMR revealed the product was a single diastereomer.

$^1$H-NMR ($C_6D_6$): δ 0.73 (d, J=6.5 Hz, 3H), 0.77 (d, J=6.5 Hz, 3H), 0.98 (s, 9H), 1.26 (m, 1H), 1.51 (m, 1H), 1.80 (m, 1H), 2.82-3.92 (m, 3H), 3.10-3.16 (m, 1H), 3.36 (s, 3H), 3.77 (d, J=9.6 Hz, 1H), 4.03 (td, J=10.0, 1.8 Hz, 1H).

$^{13}$C-NMR ($C_6D_6$): δ 21.0, 22.8, 24.0, 25.2, 40.4, 40.2, 45.0, 52.9, 56.6, 61.0, 77.1, 171.7.

EXAMPLE 7

Preparation of (S,S$_S$)-2-[1-(tert-butylsulfinylamino)butyl]-N-methyl-1,3-dithiolane-2-carboxamide

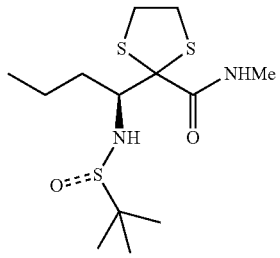

A heavy-walled glass tube was charged with ethyl (S,S$_S$)-2-[1-(tert-butylsulfinylamino)butyl]-1,3-dithiolane-2-carboxylate (0.50 g, 1.4 mmol) and a chilled 8.0 M solution of methylamine in ethanol (5 mL, 40 mmol). The mixture was allowed to warm to room temperature and was allowed to stand for 72 hours. Distillation of the solvent at reduced pressure afforded (S,S$_S$)-2-[1-(tert-butylsulfinylamino)butyl]-N-methyl-1,3-dithiolane-2-carboxamide (0.47 g, 98%) as a viscous amber-colored oil.

$^1$H-NMR (500 MHz, CD$_3$OD): δ 0.89 (t, J=7 Hz, 3H), 1.22 (s, 9H), 1.34 (m, 1H), 1.50 (m, 1H), 1.59 (m, 1H), 2.75 (s, 3H), 3.19 (m, 2H), 3.40 (m, 2H), 3.91 (m, 1H).

$^{13}$C-NMR (125 MHz, CD$_3$OD): δ 14.2, 21.3, 24.7, 27.4, 37.8, 41.0, 41.2, 58.4, 64.7, 78.7, 174.2.

EXAMPLE 8

Preparation of (S,S$_S$)-2-[1-(tert-butylsulfinylamino)-2-cyclopropylethyl]-N-methyl-1,3-dithiolane-2-carboxamide

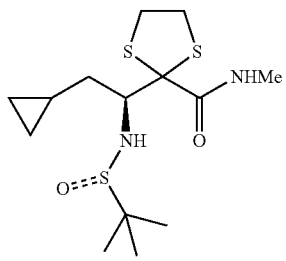

A heavy-walled glass tube was charged with ethyl (S,S$_S$)-2-[1-(tert-butylsulfinylamino)-2-cyclopropylethyl]-1,3-dithiolane-2-carboxylate (2.00 g, 5.47 mmol) and a chilled 8.0 M solution of methylamine in ethanol (5 mL, 40 mmol). The mixture was allowed to warm to room temperature and was stirred for 2 hours at which time reaction was complete by HPLC analysis. Distillation of the solvent at reduced pressure afforded the title compound (1.79 g, 93%) as an amber glass.

$^1$H-NMR (500 MHz, DMSO-d$_6$): δ 7.38 (s, 1H), 4.06-4.00 (m, 2H), 3.97-3.88 (m, 1H), 3.45-3.40 (m, 1H), 3.34-2.95 (m, 2H), 2.77 (s, 3H) 1.60-1.54 (m, 1H), 1.15 (s, 9 H), 1.05-0.99 (m, 1H), 0.83-0.74 (m, 1H), 0.46-0.40 (m, 1H), 0.35-0.30 (m, 1H), 0.06-0.03 (m, 2H).

$^{13}$C-NMR (125 MHz, DMSO-d$_6$): δ 171.0, 77.2, 63.2, 56.0, 40.1, 39.9, 26.8, 22.5, 9.1, 5.9, 4.1.

EXAMPLE 9

Preparation of (S,S$_S$)-2-[1-(4-methylphenylsulfinylamino)-2-methylbutyl]-N-methyl-1,3-dithiolane-2-carboxamide

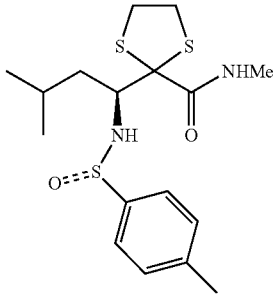

A heavy-walled glass tube was charged with ethyl (S,S$_S$)-2-[1-(4-methylphenylsulfinylamino)-2-methylbutyl]-1,3-dithiolane-2-carboxylate (0.60 g, 1.6 mmol) and a chilled 8.0 M solution of methylamine in ethanol (6 mL, 48 mmol). The mixture was allowed to warm and was maintained at room temperature for 16 h. Distillation of the solvent at reduced pressure afforded a yellowish oil. The residue was taken up in methanol (2 mL) and was allowed to stand for 30 min whereupon (S,S$_S$)-2-[1-(4-methylphenylsulfinylamino)-2-methylbutyl]-N-methyl-1,3-dithiolane-2-carboxamide separated as white crystals (0.34 g, 59%), which were collected by filtration and dried in high vacuum. MP 147-154° C.

$^1$H-NMR (500 MHz, DMSO-d$_6$): δ 0.83 (d, J=6.5, 3H), 0.84 (d, J=6.5, 3H), 1.12 (m, 1H), 1.50 (m, 1H), 1.82 (m, 1H), 2.36 (s, 3H), 2.61 (s, 3H), 3.16-3.39 (m, 4H), 4.01 (dd, J=10.6, 1.9, 1H), 7.33 (d, J=8.1 Hz, 2H), 7.52 (d, J=8.1 Hz, 2H).

$^{13}$C-NMR (125 MHz, DMSO-d$_6$): δ 20.76, 20.87, 23.64, 23.71, 26.6, 42.5, 60.4, 77.5, 125.2, 129.1, 140.1, 144.0, 170.8.

EXAMPLE 10

Preparation of (S,S$_S$)-2-[1-(tert-butylsulfinylamino)butyl]-N-cyclopropyl-1,3-dithiolanecarboxamide

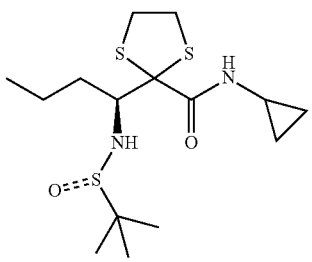

A flask was charged with ethyl (S,S$_S$)-2-[1-tert-butylsulfinylamino)butyl-1,3-dithiolanecarboxylate (1.41 g, 4.00 mmol), methanol (9.6 mL), and water (1.6 mL). Lithium hydroxide (0.19 g, 7.93 mmol) was added and the mixture was stirred for 4.5 hours at room temperature, after which it was added to water (25 mL) and was acidified with 1 N HCl (9.0 mL, 9.0 mmol). The product was extracted into dichloromethane (twice, 20 mL each time) and was dried over sodium sulfate. Removal of the solvent at reduced pressure afforded (S,S$_S$)-2-[1-tert-butylsulfinylamino)butyl-1,3-dithiolanecarboxylic acid (1.14 g, 88%) as a crisp off-white solid.

$^1$H-NMR (500 MHz, CDCl$_3$): δ 0.82 (t, J=7.0 Hz, 3H), 1.12-1.35 (m, 2H), 1.19 (s, 9H), 1.51 (m, 2H), 3.32-3.63 (m, 4H), 3.74 (m, 1H), 4.59 (d, J=9.8 Hz, 1H).

$^{13}$C-NMR (125 MHz, CDCl$_3$): δ 13.6, 20.5, 22.9, 38.1, 40.12, 40.14, 57.7, 63.5, 75.5, 173.7.

A flask was charged with a portion of the just obtained crisp off-white solid (0.94 g, 2.9 mmol), triethylamine (2.4 mL, 17 mmol), and dichloromethane (9.4 mL). The mixture was cooled to 0° C. and a 50% w/w solution of propylphosphonic anhydride in ethyl acetate (2.76 g, 4.3 mmol) was added. After 1 hour at 0° C., cyclopropylamine (300 μL, 4.3 mmol) was added and the mixture was allowed to warm to room temperature overnight. The mixture was added to 50 mL of water and the product was extracted into dichloromethane (25 mL) and dried over sodium sulfate. Distillation of solvent at reduced pressure afforded (S,S$_S$)-2-[1-(tert-butylsulfinylamino)butyl]-N-cyclopropyl-1,3-dithiolanecarboxamide (1.00 g, 95%) as yellow oil.

$^1$H-NMR (500 MHz, CDCl$_3$): δ 0.48 (m, 2H), 0.74 (d, J=7.0 Hz, 2H), 0.81 (t, J=6.5 Hz, 3H), 1.05-1.55 (m, 4H), 1.16 (s, 9H), 2.67 (m, 1H), 3.12-3.46 (m, 4H), 3.87 (td, J=9.6, 2.3 Hz, 1H), 4.05 (d, J=9.5 Hz, 1H), 7.43 (d, J=2.7 Hz, 1H).

$^{13}$C-NMR (125 MHz, CDCl$_3$): δ 6.4, 6.6, 13.6, 20.0, 22.7, 22.9, 37.4, 39.85, 39.91, 56.9, 63.5, 77.0, 172.4.

EXAMPLE 11

Preparation of (S)-2-[1-amino-3-methylbutyl]-N-methyl-1,3-dithiolane-2-carboxamide hydrochloride

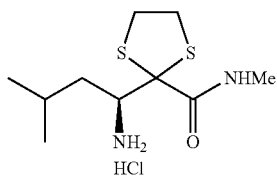

A 4.0 M solution of hydrogen chloride in dioxane (21 mL, 84 mmol) was added to a flask containing (S,S$_S$)-2-[1-tert-butylsulfinylamino)-3-methylbutyl]-N-methyl-1,3-dithiolane-2-carboxamide (2.43 g, 6.89 mmol). The mixture was stirred for 1 h, was filtered to remove a trace of cloudiness, and was added dropwise to diethyl ether (100 mL) with stirring. The precipitate was collected by filtration and dried in high vacuum to afford (S)-2-[1-amino-3-methylbutyl]-N-methyl-1,3-dithiolane-2-carboxamide hydrochloride (1.59 g, 93%) as a yellowish solid.

$^1$H NMR (500 MHz, CD$_3$OD): δ 0.94 (d, J=5.1, 3H), 0.96 (d, J=5.1, 3H), 1.26 (m, 1H), 1.60 (m, 1H), 1.79 (m, 1H), 2.79 (s, 3H), 3.40-3.58 (m, 4H), 3.97 (dd, J=9.9, 2.0, 1H).

$^{13}$C-NMR (125 MHz, CD$_3$OD): δ 21.4, 24.0, 26.0, 27.6, 41.1, 41.7, 42.1, 56.6, 75.3, 172.1.

EXAMPLE 12

Preparation of (S)-2-[1-aminobutyl]-N-cyclopropyl-1,3-dithiolane-2-carboxamide hydrochloride

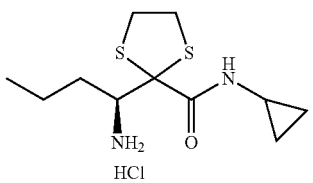 [SMILES: CCC[C@H](N)C1(C(=O)NC2CC2)SCCS1 ; Cl]

A 4.0 M solution of hydrogen chloride in dioxane (5.5 mL, 22 mmol) was added to a flask containing (S,S$_s$)-2-[1-tert-butylsulfinylamino)butyl]-N-cyclopropyl-1,3-dithiolane-2-carboxamide (1.00 g, 2.74 mmol). The mixture was allowed to stand for 1 hour at room temperature whereupon the resulting solution was added dropwise to ether (30 mL) with stirring. A solid separated. The supernatant was decanted and the solid was triturated with an additional 25 mL of ether. The product was collected by filtration and dried (30° C., 8 torr) to afford (S)-2-[1-aminobutyl]-N-cyclopropyl-1,3-dithiolane-2-carboxamide hydrochloride (0.56 g, 69%) as a pale yellow solid.

$^1$H-NMR (500 MHz, CD$_3$OD): δ 0.61 (m, 2H), 0.76 (m, 2H), 0.93 (t, 3H, J=7), 1.34-1.73 (m, 4H), 2.68 (m, 1H), 3.36-3.63 (m, 4H), 3.91 (m, 1H).

$^{13}$C-NMR (125 MHz, CD$_3$OD): δ 6.7, 6.9, 14.2, 20.7, 24.6, 35.3, 41.2, 42.0, 58.2, 74.8, 173.2.

EXAMPLE 13

Preparation of (S)-2-[1-amino-2-cyclopropylethyl]-N-methyl-1,3-dithiolane-2-carboxamide hydrochloride

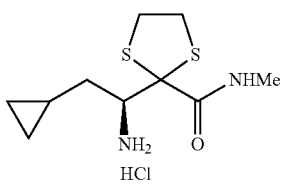 [SMILES: CNC(=O)C1([C@@H](N)CC2CC2)SCCS1 ; Cl]

A 4.0 M solution of hydrogen chloride in dioxane (5.5 mL, 22 mmol) was added to a flask containing (S,S$_S$)-2-[1-tert-butylsulfinylamino)-2-cyclopropylethyl]-N-methyl-1,3-dithiolane-2-carboxamide (1.00 g, 2.85 mmol). The mixture was stirred for 1 hour at room temperature whereupon the resulting solution was added dropwise to methyl tert-butyl ether (50 mL) with stirring. A solid separated which was washed with additional MTBE and dried in vacuo to afford (S)-2-[1-amino-2-cyclopropylethyl]-N-methyl-1,3-dithiolane-2-carboxamide hydrochloride (712 mg, 88%) as a yellow solid. MP: 75-76° C. [α]$_D^{24}$ −6.85 (H$_2$O, c=2.22).

$^1$H-NMR (500 MHz, CD$_3$OD) δ 3.82-3.77 (m, 1H), 3.35-3.21 (m, 4H), 3.31-3.10 (m, 1H), 2.57 (s, 3H), 1.51-1.44 (m, 1H), 1.17-1.11 (m, 1H), 0.67-0.60 (m, 1H), 0.43-0.31 (m, 2H), 0.03-0.11 (m, 2H).

$^{13}$C-NMR (125 MHz, CD$_3$OD): 171.2, 74.4, 59.4, 41.8, 41.1, 37.8, 27.5, 8.7, 6.4, 4.8.

EXAMPLE 14

Preparation of ethyl (S,S$_s$)-2-[(tert-butylsulfinylamino)-2-deuterio-(2-naphthyl)methyl]-1,3-dithiolane-2-carboyxlate

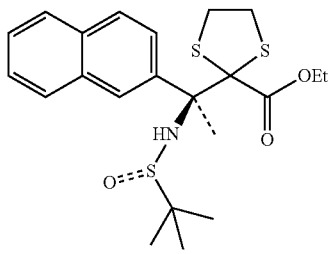

A flask was charged with ethyl 1,3-dithiolane-2-carboxylate (0.23 g, 1.3 mmol) and [N(E),S(S)]—N-[deuterio-(2-naphthyl)methylene]-2-methyl-propane-2-sulfinamide (0.33 g, 1.3 mmol) in tetrahydrofuran (5.0 mL) under a nitrogen atmosphere. The solution was cooled to −78° C. whereupon a 1.0 M solution of lithium bis(trimethylsilyl)amide in THF (1.5 mL, 1.5 mmol) was added dropwise. The mixture was stirred for 2 hours at −78° C. and was then added to half-saturated aqueous ammonium chloride (30 mL) and the product was extracted into ethyl acetate (twice, 15 mL each time). After drying over sodium sulfate, the solvent was removed at reduced pressure. The crude product was purified by flash chromatography, eluting with 4:1 ethyl acetate/hexanes. Distillation of solvent afforded ethyl (S,S$_s$)-2-[(tert-butylsulfinylamino)-2-deuterio-(2-naphthyl)methyl]-1,3-dithiolane-2-carboyxlate (0.41 g, 74%) as a colorless oil.

$^1$H-NMR (500 MHz, CDCl$_3$): δ 1.10 (s, 9H), 1.12 (t, J=7.3, 3H), 3.14-3.27 (m, 4H), 4.04 (m, 2H), 4.52 (s, 1H), 7.36-7.41 (m, 2H), 7.49 (m, 1H), 7.68-7.74 (m, 3H), 7.79 (s, 1H).

$^{13}$C-NMR (125 MHz, CDCl$_3$): δ 13.9, 22.5, 40.1, 40.4, 56.3, 62.8, 63.3 (1:1:1 triplet, J[$^2$H-$^{13}$C]=20.7 Hz), 77.0, 126.17, 126.24, 126.4, 127.6, 127.8, 128.2, 128.9, 132.8, 133.5, 135.0, 170.2.

EXAMPLE 15

Attachment of Protected α-keto Amide to Peptide

A solution of a peptide containing a carboxylic acid terminus (HOOC-Pep.) in dichloromethane was cooled to 0° C. To this chilled solution were added 1-hydroxybenzotriazole, N-methylmorpholine, and N-(3-dimethylaminopropyl)-N'-ethylcarbodiimide hydrochloride, followed by the addition of (S)-2-[1-amino-2-cyclopropylethyl]-N-methyl-1,3-dithiolane-2-carboxamide hydrochloride as a solid (obtained from Example 13). The completion level of the reaction was monitored by HPLC analysis (e.g., in 2.5 hours). The reaction mixture was stirred for an extended period of time after the completion of the reaction before it was quenched with water and the organic phase washed with 1 M HCl and 5% aqueous sodium bicarbonate solution. The product (protected alpha-ketoamide peptide) was recovered from the organic phase and its purity was determined by HPLC analysis and NMR.

EXAMPLE 16

Deprotection of α-keto Amide in Peptide

The protected alpha-ketoamide peptide product from Example 15 was dissolved in dichloromethane. Water was added to the solution and the resultant biphasic mixture was stirred at 0° C. Solid N-bromosuccinimide was then added to the reaction mixture in three portions over the course of 140 minutes. After 155 minutes or HPLC analysis indicated that the reaction was complete, the reaction mixture was quenched with 1 M aqueous sodium bisulfite. To break the resulting emulsion, 5% sodium chloride and glacial acetic acid were added and the organic phase was separated. After distillation of the solvent, HPLC analysis was used to ensure none of the undesired diastereomer was present. The residue was purified by flash chromatography eluting with a mixture of hexanes and ethyl acetate, and the product-containing cuts were concentrated and the concentrate was re-dissolved in acetonitrile. After stirring for 72 hours, the precipitate was collected by filtration, washed with acetonitrile, and dried on the frit to afford a peptide product in which the protecting disulfide group was removed.

EXAMPLE 17

Coupling of Protected α-keto Amide with Cbz-Proline to Form Protected Dipeptide

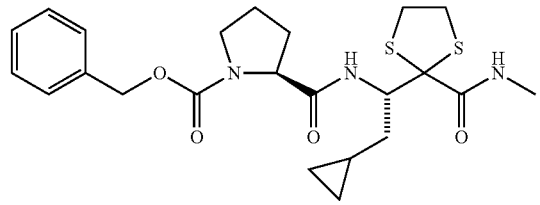 [SMILES: CNC(=O)C1([C@H](CC2CC2)NC(=O)[C@@H]2CCCN2C(=O)OCc2ccccc2)SCCS1]

A mixture of (−)-carbobenzyloxy-(L)-proline (3.66 g, 14.7 mmol), dichloromethane (37 mL), and hydroxybenzotriazole hydrate (2.25 g, 14.7 mmol) was cooled to 0° C. To the cooled mixture were added N-methylmorpholine (2.97 g, 29.4 mmol), N-(3-dimethylaminopropyl)-N'-ethylcarbodiimide hydrochloride (3.94 g, 20.6 mmol) and (S)-2-[1-amino-2-cyclopropylethyl]-N-methyl-1,3-dithiolane-2-carboxamide hydrochloride (5.08 g, 16.2 mmol, prepared according to Example 13). The mixture was stirred for 18 hours and then quenched with water (40 mL). After phase separation, the organic phase was washed with aqueous sodium bicarbonate (5 w/w % solution, 40 mL) and 1 N HCl (40 mL). The organic phase was then concentrated by rotary evaporation and dried for 4 hours under high vacuum, furnishing 7.00 g of the dipeptide shown above [(S)-benzyl 2-((S)-2-cyclopropyl-1-(2-(methylcarbamoyl)-1,3-dithiolan-2-yl)ethylcarbamoyl) pyrrolidine-1-carboxylate] as white foam which still contained some solvent. An analytical sample was further dried and characterized.

$^1$H NMR (500 MHz, DMSO-d$_6$): δ 8.00-8.05 (m, 1H), 7.50-7.65 (m, 1H), 7.24-7.39 (m, 5H), 5.04-5.10 (m, 1.5H, part of a mixture of two rotamers), 4.89 (d, 0.5H, J=20 Hz, part of a mixture of two rotamers), 4.65-4.74 (m, 1H), 4.35-4.45 (m, 1H), 3.35-3.50 (m, 2H), 3.15-3.32 (m, 4H), 2.60-2.64 (m, 3H), 2.02-2.18 (m, 1H), 1.76-1.96 (m, 3H), 1.34-1.43 (m, 1H), 1.00-1.07 (m, 0.5H, part of a mixture of two rotamers), 0.86-0.93 (m, 0.5H, part of a mixture of two rotamers), 0.61-0.68 (m, 0.5H, part of a mixture of two rotamers), 0.40-0.47 (m, 0.5H, part of a mixture of two rotamers), 0.33-0.40 (m, 0.5H, part of a mixture of two rotamers), 0.22-0.28 (m, 0.5H, part of a mixture of two rotamers), 0.02-0.11 (m, 1.5H, part of a mixture of two rotamers), −0.12~−0.02 (m, 1.5H, part of a mixture of two rotamers).

$^{13}$C NMR (125 MHz, DMSO-d$_6$): δ 171.7, 171.4, 170.7, 154.2, 153.9, 137.1, 128.3, 128.1, 127.7, 127.4, 126.8, 76.1, 65.8, 65.6, 59.9, 59.2, 54.7, 54.5, 47.1, 46.5, 38.3, 38.2, 31.3, 29.8, 26.9, 23.9, 22.9, 8.4, 4.8, 4.7, 4.1, 4.0.

EXAMPLE 18

Deprotection of Dithiolate to Release α-keto Amide-Containing Dipeptide

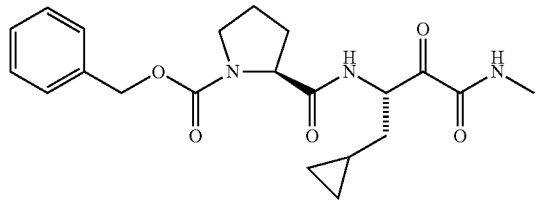 [SMILES: CNC(=O)C(=O)[C@H](CC1CC1)NC(=O)[C@@H]1CCCN1C(=O)OCc1ccccc1]

Water (2.0 mL) and 5,5-dimethyl-1,3-dibromohydantoin (2.34 g, 8.20 mmol) were added in that order to a solution of the protected dipeptide obtained from Example 17 (1.00 g, 2.05 mmol) in acetonitrile (20 mL). The resulting orange solution was stirred for 1 hour, at which time the reaction was determined to be complete by HPLC. Isopropyl acetate (35 mL) was added to the solution to give a mixture which was then washed with a solution of sodium thiosulfate (4.32 g, 17.2 mmol) in water (20 mL) to give a colorless organic phase. The organic phase was washed with aqueous sodium bicarbonate (5 w/w % solution, 2 '50 mL) and was analyzed by HPLC to ensure complete removal of hydantoin by-products. The remaining mixture was concentrated by rotary evaporation to give an oily residue and the resulting oil was dried under high vacuum to yield the deprotected dipeptide shown above [(S)-benzyl 2-((S)-1-cyclopropyl-4-(methylamino)-3,4-dioxobutan-2-ylcarbamoyl)pyrrolidine-1-carboxylate] as a white waxy solid (0.55 g, 64% yield for two steps).

$^1$H NMR (500 MHz, DMSO-d$_6$): δ 8.59-8.61 (m, 1H), 8.35-8.39 (m, 1H), 7.28-7.37 (m, 5H), 5.00-5.06 (m, 3H), 4.33 (dd, 0.6H, J=8.0, 2.5 Hz, part of a mixture of two rotamers), 4.28 (dd, 0.4H, J=8.0, 2.5 Hz, part of a mixture of two rotamers), 3.33-3.45 (m, 2H), 2.64 (d, 3H, J=5.0 Hz), 2.09-2.19 (m, 1H), 1.75-1.86 (m, 3H), 1.68 (ddd, 0.4H, J=14.0, 8.0, 6.0 Hz, part of a mixture of two rotamers), 1.60 (ddd, 0.6H, J=14.0, 8.0, 6.0 Hz, part of a mixture of two rotamers), 1.37-1.49 (m, 1H), 0.77-0.85 (m, 0.4H, part of a mixture of two rotamers), 0.65-0.73 (m, 0.5H, part of a mixture of two rotamers), 0.21-0.44 (m, 2H), −0.05~0.09 (m, 2H).

$^{13}$C NMR (125 MHz, DMSO-d$_6$): δ 196.9, 172.2, 171.9, 161.2, 161.1, 153.9, 153.7, 137.0, 136.9, 128.4, 128.1, 127.7, 127.5, 127.4, 126.9, 65.8, 59.2, 58.7, 54.5, 54.5, 47.1, 46.4, 34.8, 31.1, 29.9, 25.4, 24.6, 23.7, 22.9, 7.9, 4.9, 4.2, 4.1.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of Formula IV or Formula VI:

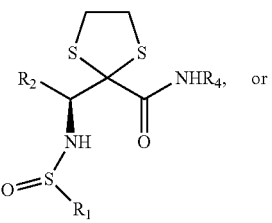

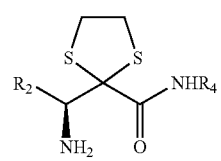

wherein:
R$_1$ is alkyl or aryl;
R$_2$ is alkyl, cycloalkyl, (cycloalkyl)alkyl, alkenyl, aryl, or heterocycloalkyl; and
R$_4$ is methyl, ethyl, or cyclopropyl.

2. The compound of claim 1, wherein R$_1$ is optionally substituted phenyl, methyl, ethyl, propyl, isopropyl, butyl, or tert-butyl.

3. The compound of claim 1, wherein R$_2$ is alkyl, (cycloalkyl)alkyl, or aryl.

4. The compound of claim 3, wherein R$_2$ is methyl, ethyl, propyl, isopropyl, butyl, isobutyl, tert-butyl, (cyclopropyl)methyl, or naphthyl.

5. The compound of claim 1, wherein the compound is

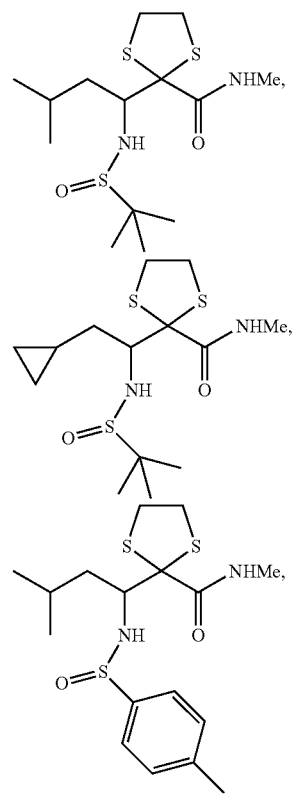

-continued
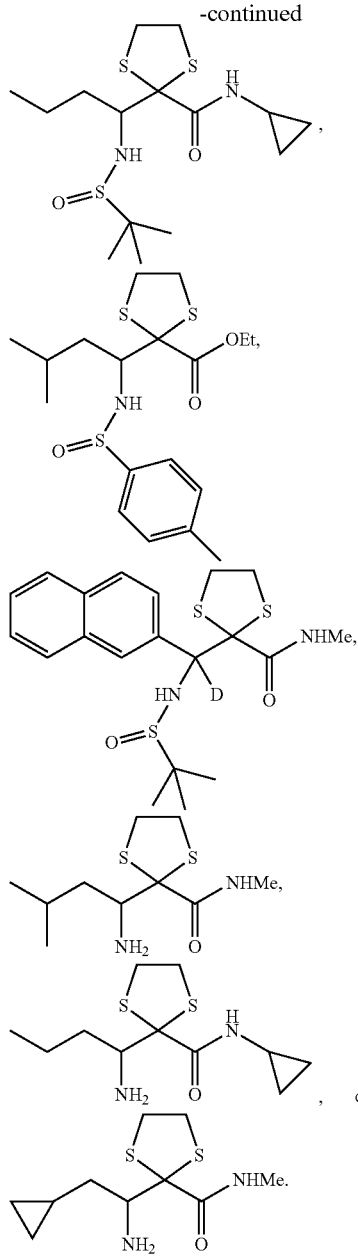
6. The compound of claim 1, wherein the compound is
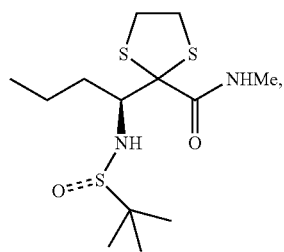
-continued
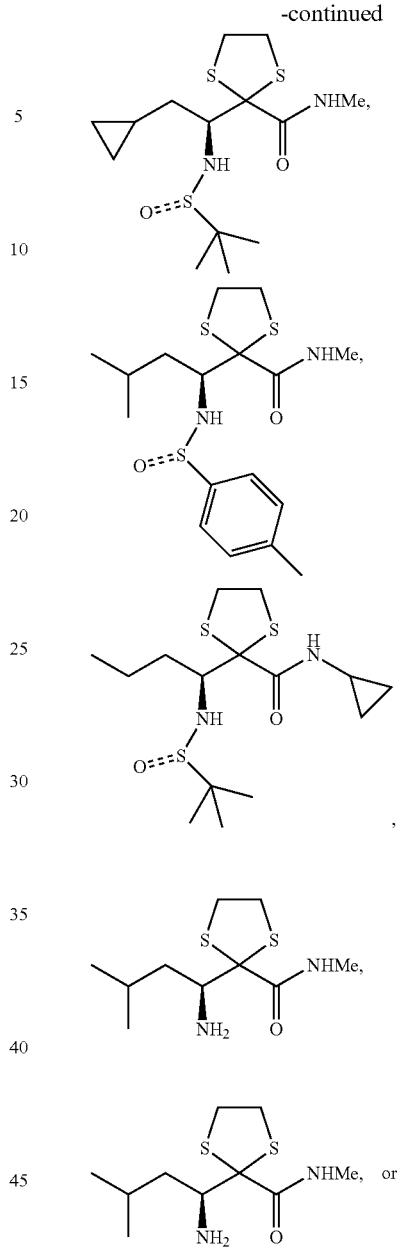
7. The compound of claim 2, wherein $R_1$ is p-methylphenyl.
* * * * *